(12) United States Patent
Swisher

(10) Patent No.: US 7,905,857 B2
(45) Date of Patent: Mar. 15, 2011

(54) NEEDLE ASSEMBLY INCLUDING OBTURATOR WITH SAFETY RESET

(75) Inventor: David Rork Swisher, St. Charles, MO (US)

(73) Assignee: Covidien AG (CH)

( * ) Notice: Subject to any disclaimer, the term of this patent is extended or adjusted under 35 U.S.C. 154(b) by 1646 days.

(21) Appl. No.: 11/179,438

(22) Filed: Jul. 11, 2005

(65) Prior Publication Data

US 2007/0073244 A1    Mar. 29, 2007

(51) Int. Cl.
*A61M 5/32* (2006.01)
(52) U.S. Cl. ......... 604/110; 604/192; 604/162; 600/567
(58) Field of Classification Search .................. 604/110, 604/162, 164.08, 192, 264, 272; 600/562, 600/564, 567
See application file for complete search history.

(56) References Cited

U.S. PATENT DOCUMENTS

| | | |
|---|---|---|
| 1,115,561 A | 11/1914 | Northey |
| 1,436,707 A | 11/1922 | Gaschke |
| 1,518,531 A | 12/1924 | Lung |
| 2,219,605 A | 6/1938 | Turkel |
| 2,854,976 A | 10/1958 | Heydrich |
| 3,254,533 A | 6/1966 | Tongret |
| 3,539,034 A | 11/1970 | Tafeen |
| 3,610,240 A | 10/1971 | Harautuneian |
| 3,681,991 A | 8/1972 | Eberly, Jr. |
| 3,729,998 A | 5/1973 | Mueller et al. |
| 3,822,598 A | 7/1974 | Hunter et al. |
| 3,884,230 A | 5/1975 | Wulff |
| 3,890,971 A | 6/1975 | Leeson et al. |
| 3,893,058 A | 7/1975 | Keith |
| 3,893,445 A | 7/1975 | Hofsess |
| 3,904,033 A | 9/1975 | Haerr |
| 3,915,003 A | 10/1975 | Adams |
| 3,946,613 A | 3/1976 | Silver |
| 3,976,070 A | 8/1976 | Dumont |
| 4,008,614 A | 2/1977 | Turner |
| 4,010,737 A | 3/1977 | Vilaghy et al. |
| 4,026,287 A | 5/1977 | Haller |
| 4,099,518 A | 7/1978 | Baylis et al. |
| D249,475 S | 9/1978 | Turner et al. |

(Continued)

FOREIGN PATENT DOCUMENTS

DE    3805567 A1    8/1989

(Continued)

OTHER PUBLICATIONS

Office Action dated Jan. 11, 2010 from related U.S. Appl. No. 11/179,696, 8 pgs. Office Action dated Feb. 3, 2010 from related U.S. Appl. No. 11/179,090, 5 pgs.
All prosecution related to U.S. Appl. No. 11/179,090, filed Jul. 11, 2005.
All prosecution related to U.S. Appl. No. 11/179,696, filed Jul. 11, 2005.

*Primary Examiner* — Nicholas D Lucchesi
*Assistant Examiner* — Laura A Bouchelle
(74) *Attorney, Agent, or Firm* — Lisa E. Winsor, Esq.

(57) ABSTRACT

A needle assembly is able to collect a sample of biological material in a needle of the assembly. The needle assembly has a safety shield capable of being moved on the needle assembly to cover a sharp tip of the needle assembly. The shield can be locked in place over the sharp tip by a locking mechanism. The assembly further includes an obturator that can be inserted into the needle to remove the sample from the needle. A reset member associated with the obturator is capable of engaging the locking mechanism to release the locking mechanism and allow the shield to be moved away from the sharp tip.

10 Claims, 16 Drawing Sheets

U.S. PATENT DOCUMENTS

| | | |
|---|---|---|
| 4,112,762 A | 9/1978 | Turner et al. |
| 4,139,009 A | 2/1979 | Alvarez |
| 4,142,517 A | 3/1979 | Stavropoulos et al. |
| 4,143,853 A | 3/1979 | Abramson |
| 4,160,450 A | 7/1979 | Doherty |
| 4,163,446 A | 8/1979 | Jamshidi |
| 4,177,797 A | 12/1979 | Baylis et al. |
| 4,183,248 A | 1/1980 | West |
| D255,997 S | 7/1980 | Maeda |
| 4,211,214 A | 7/1980 | Chikashige |
| 4,256,119 A | 3/1981 | Gauthier |
| 4,258,713 A | 3/1981 | Wardlaw |
| 4,258,722 A | 3/1981 | Sessions et al. |
| 4,262,676 A | 4/1981 | Jamshidi |
| 4,266,543 A | 5/1981 | Blum |
| 4,266,555 A | 5/1981 | Jamshidi |
| 4,314,565 A | 2/1982 | Lee |
| 4,356,828 A | 11/1982 | Jamshidi |
| 4,392,859 A | 7/1983 | Dent |
| 4,403,617 A | 9/1983 | Tretinyak |
| 4,425,120 A | 1/1984 | Sampson |
| 4,438,884 A | 3/1984 | O'Brien et al. |
| 4,469,109 A | 9/1984 | Mehl |
| 4,482,348 A | 11/1984 | Dent |
| 4,487,209 A | 12/1984 | Mehl |
| 4,513,754 A | 4/1985 | Lee |
| 4,543,966 A | 10/1985 | Islam et al. |
| 4,572,365 A | 2/1986 | Bruno et al. |
| 4,573,976 A | 3/1986 | Sampson |
| 4,613,329 A | 9/1986 | Bodicky |
| 4,619,271 A | 10/1986 | Burger et al. |
| 4,630,616 A | 12/1986 | Tretinyak |
| 4,631,057 A | 12/1986 | Mitchell |
| 4,639,249 A | 1/1987 | Larson |
| 4,642,785 A | 2/1987 | Packard |
| 4,643,199 A | 2/1987 | Jennings |
| 4,643,200 A | 2/1987 | Jennings |
| 4,655,226 A | 4/1987 | Lee |
| 4,664,654 A | 5/1987 | Strauss |
| 4,676,783 A | 6/1987 | Jagger et al. |
| 4,681,567 A | 7/1987 | Masters |
| 4,693,708 A | 9/1987 | Wanderer |
| 4,695,274 A | 9/1987 | Fox |
| D292,493 S | 10/1987 | King |
| D292,494 S | 10/1987 | King |
| D293,215 S | 12/1987 | Bruno et al. |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry |
| 4,737,144 A | 4/1988 | Choksi |
| 4,738,663 A | 4/1988 | Bogan |
| 4,741,627 A | 5/1988 | Fukui |
| 4,743,233 A | 5/1988 | Schneider |
| 4,747,831 A | 5/1988 | Kulli |
| 4,747,836 A | 5/1988 | Luther |
| 4,747,837 A | 5/1988 | Hauck |
| 4,752,290 A | 6/1988 | Schramm |
| 4,762,516 A | 8/1988 | Luther |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,785,826 A | 11/1988 | Ward |
| 4,790,329 A | 12/1988 | Simon |
| 4,790,827 A | 12/1988 | Haber et al. |
| 4,790,828 A | 12/1988 | Dombrowski |
| 4,793,363 A | 12/1988 | Ausherman et al. |
| 4,795,432 A | 1/1989 | Karczmer |
| 4,804,371 A | 2/1989 | Vaillancourt |
| 4,804,372 A | 2/1989 | Laico |
| 4,810,248 A | 3/1989 | Masters |
| 4,813,426 A | 3/1989 | Haber et al. |
| 4,816,022 A | 3/1989 | Poncy |
| D300,728 S | 4/1989 | Ross |
| 4,819,659 A | 4/1989 | Sitar |
| 4,820,275 A | 4/1989 | Haber et al. |
| 4,826,488 A | 5/1989 | Nelson |
| 4,826,490 A | 5/1989 | Byrne et al. |
| 4,826,491 A | 5/1989 | Schramm |
| 4,834,718 A | 5/1989 | McDonald |
| 4,838,280 A | 6/1989 | Haaga |
| 4,838,282 A | 6/1989 | Strasser et al. |
| 4,842,586 A | 6/1989 | Hogan |
| 4,846,809 A | 7/1989 | Sims |
| 4,900,307 A | 2/1990 | Kulli |
| 4,904,242 A | 2/1990 | Kulli |
| 4,906,235 A | 3/1990 | Roberts |
| 4,909,793 A | 3/1990 | Vining |
| 4,911,694 A | 3/1990 | Dolan |
| 4,911,706 A | 3/1990 | Levitt |
| 4,915,702 A | 4/1990 | Haber |
| D307,558 S | 5/1990 | Messina et al. |
| 4,922,602 A | 5/1990 | Mehl |
| 4,927,414 A | 5/1990 | Kulli |
| 4,929,241 A | 5/1990 | Kulli |
| 4,931,044 A | 6/1990 | Beiter |
| 4,935,013 A | 6/1990 | Haber et al. |
| 4,943,283 A | 7/1990 | Hogan |
| 4,944,725 A | 7/1990 | McDonald |
| 4,950,250 A | 8/1990 | Haber |
| 4,952,207 A | 8/1990 | Lemieux |
| 4,955,866 A | 9/1990 | Corey |
| 4,958,625 A | 9/1990 | Bates et al. |
| 4,960,412 A | 10/1990 | Fink |
| 4,964,854 A | 10/1990 | Luther |
| 4,966,587 A | 10/1990 | Baumgart |
| 4,969,554 A | 11/1990 | Sawaya |
| 4,978,344 A | 12/1990 | Dombrowski |
| 4,986,279 A | 1/1991 | O'Neill |
| 4,994,041 A | 2/1991 | Dombrowski |
| 5,005,585 A | 4/1991 | Mazza |
| 5,012,818 A | 5/1991 | Joishy |
| 5,013,304 A | 5/1991 | Russell et al. |
| 5,031,634 A | 7/1991 | Simon |
| 5,036,860 A | 8/1991 | Leigh et al. |
| 5,047,044 A | 9/1991 | Smith et al. |
| 5,049,136 A | 9/1991 | Johnson |
| 5,051,109 A | 9/1991 | Simon |
| 5,053,017 A | 10/1991 | Chamuel |
| 5,057,085 A | 10/1991 | Kopans |
| 5,059,180 A | 10/1991 | McLees |
| 5,085,648 A | 2/1992 | Purdy et al. |
| 5,092,851 A | 3/1992 | Ragner |
| 5,102,394 A | 4/1992 | Lasaitis |
| 5,108,374 A | 4/1992 | Lemieux |
| 5,126,090 A | 6/1992 | Egolf et al. |
| 5,127,916 A | 7/1992 | Spencer et al. |
| 5,133,727 A | 7/1992 | Bales et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,172,702 A | 12/1992 | Leigh et al. |
| 5,176,256 A | 1/1993 | Sawaya |
| 5,183,468 A | 2/1993 | McLees |
| 5,195,533 A | 3/1993 | Chin et al. |
| 5,195,985 A | 3/1993 | Hall |
| 5,213,115 A | 5/1993 | Zytkovicz et al. |
| 5,215,525 A | 6/1993 | Sturman |
| 5,215,528 A | 6/1993 | Purdy et al. |
| 5,215,533 A | 6/1993 | Robb |
| 5,217,438 A | 6/1993 | Davis |
| 5,228,451 A | 7/1993 | Bales et al. |
| 5,256,149 A | 10/1993 | Banik et al. |
| 5,257,632 A | 11/1993 | Turkel et al. |
| 5,279,306 A | 1/1994 | Mehl |
| 5,279,563 A | 1/1994 | Brucker et al. |
| 5,279,591 A | 1/1994 | Simon |
| 5,282,477 A | 2/1994 | Bauer |
| 5,295,977 A | 3/1994 | Cohen et al. |
| 5,304,136 A | 4/1994 | Erskine |
| 5,312,359 A | 5/1994 | Wallace |
| 5,314,406 A | 5/1994 | Arias et al. |
| 5,316,013 A | 5/1994 | Striebel, II et al. |
| 5,320,635 A | 6/1994 | Smith |

| | | | | | | |
|---|---|---|---|---|---|---|
| 5,322,517 A | 6/1994 | Sircom et al. | | 5,578,015 A | 11/1996 | Robb |
| 5,324,288 A | 6/1994 | Billings et al. | | 5,584,809 A | 12/1996 | Gaba |
| 5,328,482 A | 7/1994 | Sircom et al. | | 5,584,810 A | 12/1996 | Brimhall |
| 5,331,971 A | 7/1994 | Bales et al. | | 5,584,818 A | 12/1996 | Morrison |
| 5,331,972 A | 7/1994 | Wadhwani et al. | | 5,586,990 A | 12/1996 | Hahnen et al. |
| 5,334,158 A | 8/1994 | McLees | | 5,591,202 A | 1/1997 | Slater et al. |
| 5,338,311 A | 8/1994 | Mahurkar | | 5,595,186 A | 1/1997 | Rubinstein et al. |
| 5,338,314 A | 8/1994 | Ryan | | 5,599,310 A | 2/1997 | Bogert |
| 5,341,816 A | 8/1994 | Allen | | 5,601,536 A | 2/1997 | Crawford et al. |
| 5,344,408 A | 9/1994 | Partika | | 5,601,585 A | 2/1997 | Banik et al. |
| 5,348,022 A | 9/1994 | Leigh et al. | | 5,601,599 A | 2/1997 | Nunez |
| 5,348,544 A | 9/1994 | Sweeney et al. | | 5,611,781 A | 3/1997 | Sircom et al. |
| 5,356,421 A | 10/1994 | Castro | | 5,615,690 A | 4/1997 | Giurtino et al. |
| 5,357,974 A | 10/1994 | Baldridge | | 5,616,135 A | 4/1997 | Thorne et al. |
| 5,368,045 A | 11/1994 | Clement et al. | | 5,623,969 A | 4/1997 | Raines |
| 5,368,046 A | 11/1994 | Scarfone et al. | | 5,624,459 A | 4/1997 | Kortenbach et al. |
| 5,370,623 A | 12/1994 | Kreamer | | 5,630,506 A | 5/1997 | Thorne et al. |
| D354,921 S | 1/1995 | Narayanan | | 5,630,837 A | 5/1997 | Crowley |
| 5,385,151 A | 1/1995 | Scarfone et al. | | 5,632,555 A | 5/1997 | Gregory |
| 5,385,570 A | 1/1995 | Chin et al. | | 5,634,473 A | 6/1997 | Goldenberg et al. |
| 5,389,104 A | 2/1995 | Hahnen et al. | | 5,643,307 A | 7/1997 | Turkel et al. |
| 5,389,106 A | 2/1995 | Tower | | 5,656,031 A | 8/1997 | Thorne et al. |
| 5,394,885 A | 3/1995 | Francese | | 5,662,610 A | 9/1997 | Sircom |
| 5,395,375 A | 3/1995 | Turkel et al. | | 5,666,965 A | 9/1997 | Bales et al. |
| 5,396,900 A | 3/1995 | Slater et al. | | 5,669,883 A | 9/1997 | Scarfone et al. |
| 5,399,167 A | 3/1995 | Deniega | | 5,672,161 A | 9/1997 | Allen |
| 5,403,283 A | 4/1995 | Luther | | 5,679,907 A | 10/1997 | Ruck |
| 5,405,323 A | 4/1995 | Rogers et al. | | 5,685,852 A | 11/1997 | Turkel et al. |
| 5,405,388 A | 4/1995 | Fox | | 5,685,862 A | 11/1997 | Mahurkar |
| 5,409,461 A | 4/1995 | Steinman | | 5,687,907 A | 11/1997 | Holden |
| 5,411,486 A | 5/1995 | Zadini | | 5,690,619 A | 11/1997 | Erskine |
| 5,415,182 A | 5/1995 | Chin et al. | | 5,693,022 A | 12/1997 | Haynes |
| 5,417,659 A | 5/1995 | Gaba | | 5,693,031 A | 12/1997 | Ryan et al. |
| 5,417,709 A | 5/1995 | Slater | | 5,695,467 A | 12/1997 | Miyata et al. |
| 5,419,766 A | 5/1995 | Chang et al. | | 5,695,521 A | 12/1997 | Anderhub |
| 5,421,522 A | 6/1995 | Bowen | | 5,697,904 A | 12/1997 | Raines et al. |
| 5,423,766 A | 6/1995 | Di Cesare | | 5,697,907 A | 12/1997 | Gaba |
| 5,425,718 A | 6/1995 | Tay | | 5,700,249 A | 12/1997 | Jenkins |
| 5,425,884 A | 6/1995 | Botz | | 5,700,250 A | 12/1997 | Erskine |
| 5,429,138 A | 7/1995 | Jamshidi | | 5,702,080 A | 12/1997 | Whittier et al. |
| 5,429,616 A | 7/1995 | Schaffer | | 5,702,369 A | 12/1997 | Mercereau |
| 5,454,378 A | 10/1995 | Palmer et al. | | 5,706,824 A | 1/1998 | Whittier |
| 5,456,267 A | 10/1995 | Stark | | 5,707,392 A | 1/1998 | Kortenbach |
| 5,458,658 A | 10/1995 | Sircom | | 5,713,368 A | 2/1998 | Leigh |
| 5,462,062 A | 10/1995 | Rubinstein et al. | | 5,713,888 A | 2/1998 | Neuenfeldt et al. |
| 5,466,223 A | 11/1995 | Bressler et al. | | 5,715,832 A | 2/1998 | Koblish et al. |
| 5,471,992 A | 12/1995 | Banik et al. | | 5,718,688 A | 2/1998 | Wozencroft |
| 5,473,629 A | 12/1995 | Muramoto | | 5,722,422 A | 3/1998 | Palmer et al. |
| 5,476,099 A | 12/1995 | Robinson et al. | | 5,730,150 A | 3/1998 | Peppel et al. |
| 5,476,102 A | 12/1995 | Como et al. | | 5,730,724 A | 3/1998 | Plishka et al. |
| 5,478,313 A | 12/1995 | White | | 5,735,827 A | 4/1998 | Adwers |
| 5,480,385 A | 1/1996 | Thorne et al. | | 5,738,660 A | 4/1998 | Luther |
| 5,482,054 A | 1/1996 | Slater et al. | | 5,738,665 A | 4/1998 | Caizza |
| 5,487,734 A | 1/1996 | Thorne et al. | | 5,746,753 A | 5/1998 | Sullivan et al. |
| 5,492,532 A | 2/1996 | Ryan et al. | | 5,752,923 A | 5/1998 | Terwilliger |
| 5,501,675 A | 3/1996 | Erskine | | D395,609 S | 6/1998 | Knieriem et al. |
| 5,507,296 A | 4/1996 | Bales et al. | | 5,758,655 A | 6/1998 | Como Rodriguez et al. |
| 5,507,297 A | 4/1996 | Slater et al. | | 5,776,157 A | 7/1998 | Thorne et al. |
| 5,507,298 A | 4/1996 | Schramm et al. | | 5,795,336 A | 8/1998 | Romano et al. |
| 5,514,100 A | 5/1996 | Mahurkar | | 5,807,275 A | 9/1998 | Jamshidi |
| 5,514,152 A | 5/1996 | Smith | | 5,807,277 A | 9/1998 | Swaim |
| 5,522,398 A | 6/1996 | Goldenberg et al. | | 5,810,744 A | 9/1998 | Chu et al. |
| 5,526,821 A | 6/1996 | Jamshidi | | 5,817,069 A | 10/1998 | Arnett |
| 5,533,516 A | 7/1996 | Sahatjian | | 5,823,970 A | 10/1998 | Terwilliger |
| 5,533,974 A | 7/1996 | Gaba | | 5,823,971 A | 10/1998 | Robinson et al. |
| 5,538,009 A | 7/1996 | Byrne et al. | | 5,823,997 A | 10/1998 | Thorne |
| 5,542,927 A | 8/1996 | Thorne et al. | | 5,824,002 A | 10/1998 | Gentelia et al. |
| 5,549,565 A | 8/1996 | Ryan et al. | | D400,806 S | 11/1998 | Tillack |
| 5,549,708 A | 8/1996 | Thorne et al. | | D400,808 S | 11/1998 | Schwan |
| 5,553,624 A | 9/1996 | Francese et al. | | 5,836,917 A | 11/1998 | Thorne et al. |
| 5,558,651 A | 9/1996 | Crawford et al. | | 5,836,921 A | 11/1998 | Mahurkar |
| 5,562,629 A | 10/1996 | Haughton | | 5,840,044 A | 11/1998 | Dassa et al. |
| 5,562,633 A | 10/1996 | Wozencroft | | 5,843,001 A | 12/1998 | Goldenberg |
| 5,562,683 A | 10/1996 | Chan | | 5,848,692 A | 12/1998 | Thorne et al. |
| 5,569,217 A | 10/1996 | Luther | | 5,853,393 A | 12/1998 | Bogert |
| 5,569,299 A | 10/1996 | Dill et al. | | 5,860,955 A | 1/1999 | Wright et al. |
| 5,570,783 A | 11/1996 | Thorne et al. | | 5,865,806 A | 2/1999 | Howell |
| 5,573,008 A | 11/1996 | Robinson et al. | | 5,871,453 A | 2/1999 | Banik et al. |
| 5,573,510 A | 11/1996 | Isaacson | | 5,873,886 A | 2/1999 | Larsen et al. |

| Patent No. | Date | Inventor(s) |
|---|---|---|
| 5,879,332 A | 3/1999 | Schwemberger et al. |
| 5,879,337 A | 3/1999 | Kuracina et al. |
| 5,879,338 A | 3/1999 | Mahurkar |
| 5,882,337 A | 3/1999 | Bogert et al. |
| 5,885,226 A | 3/1999 | Rubinstein et al. |
| 5,891,105 A | 4/1999 | Mahurkar |
| 5,893,845 A | 4/1999 | Newby |
| 5,893,876 A | 4/1999 | Turkel et al. |
| 5,895,361 A | 4/1999 | Turturro |
| 5,897,507 A | 4/1999 | Kortenbach et al. |
| 5,906,594 A | 5/1999 | Scarfone et al. |
| 5,910,130 A | 6/1999 | Caizza et al. |
| 5,910,132 A | 6/1999 | Schultz |
| 5,911,705 A | 6/1999 | Howell |
| 5,913,859 A | 6/1999 | Shapira |
| 5,916,175 A | 6/1999 | Bauer |
| 5,928,162 A | 7/1999 | Giurtino et al. |
| 5,928,163 A | 7/1999 | Roberts et al. |
| 5,928,200 A | 7/1999 | Thorne et al. |
| 5,935,109 A | 8/1999 | Donnan |
| 5,947,930 A | 9/1999 | Schwemberger et al. |
| 5,951,489 A | 9/1999 | Bauer |
| 5,951,525 A | 9/1999 | Thorne et al. |
| 5,951,582 A | 9/1999 | Thorne et al. |
| 5,954,696 A | 9/1999 | Ryan |
| 5,954,698 A | 9/1999 | Pike |
| 5,957,863 A | 9/1999 | Koblish et al. |
| 5,957,887 A | 9/1999 | Osterlind et al. |
| 5,957,892 A | 9/1999 | Thorne |
| 5,961,526 A | 10/1999 | Chu et al. |
| 5,961,534 A | 10/1999 | Banik et al. |
| 5,964,717 A | 10/1999 | Gottlieb et al. |
| 5,967,490 A | 10/1999 | Pike |
| 5,976,115 A | 11/1999 | Parris et al. |
| 5,979,840 A | 11/1999 | Hollister et al. |
| 5,980,488 A | 11/1999 | Thorne |
| 5,989,196 A | 11/1999 | Chu et al. |
| 5,989,229 A | 11/1999 | Chiappetta |
| 5,989,241 A | 11/1999 | Plishka et al. |
| 5,993,426 A | 11/1999 | Hollister |
| 6,000,846 A | 12/1999 | Gregory et al. |
| 6,001,080 A | 12/1999 | Kuracina et al. |
| 6,004,294 A | 12/1999 | Brimhall et al. |
| 6,007,560 A | 12/1999 | Gottlieb et al. |
| 6,015,391 A | 1/2000 | Rishton et al. |
| 6,022,324 A | 2/2000 | Skinner |
| 6,024,708 A | 2/2000 | Bales et al. |
| 6,024,727 A | 2/2000 | Thorne et al. |
| 6,033,369 A | 3/2000 | Goldenberg |
| 6,036,361 A | 3/2000 | Gregory et al. |
| 6,036,675 A | 3/2000 | Thorne et al. |
| 6,047,729 A | 4/2000 | Hollister et al. |
| 6,050,954 A | 4/2000 | Mittermeier |
| 6,050,976 A | 4/2000 | Thorne et al. |
| 6,053,877 A | 4/2000 | Banik et al. |
| 6,063,037 A | 5/2000 | Mittermeier et al. |
| 6,063,040 A | 5/2000 | Owen et al. |
| 6,071,284 A | 6/2000 | Fox |
| 6,080,115 A | 6/2000 | Rubinstein |
| 6,083,176 A | 7/2000 | Terwilliger |
| 6,083,202 A | 7/2000 | Smith |
| 6,086,563 A | 7/2000 | Moulton et al. |
| 6,090,078 A | 7/2000 | Erskine |
| 6,090,108 A | 7/2000 | McBrayer et al. |
| 6,095,967 A | 8/2000 | Black et al. |
| 6,096,005 A | 8/2000 | Botich |
| 6,102,920 A | 8/2000 | Sullivan et al. |
| 6,106,484 A | 8/2000 | Terwilliger |
| 6,110,128 A | 8/2000 | Andelin et al. |
| 6,110,129 A | 8/2000 | Terwilliger |
| 6,110,176 A | 8/2000 | Shapira |
| RE36,885 E | 9/2000 | Blecher et al. |
| 6,117,108 A | 9/2000 | Woehr et al. |
| 6,117,112 A | 9/2000 | Mahurkar |
| 6,117,115 A | 9/2000 | Hill et al. |
| 6,132,401 A | 10/2000 | Van Der Meyden |
| 6,135,110 A | 10/2000 | Roy |
| 6,142,956 A | 11/2000 | Kortenbach et al. |
| 6,142,957 A | 11/2000 | Diamond et al. |
| 6,149,629 A | 11/2000 | Wilson et al. |
| 6,171,284 B1 | 1/2001 | Kao |
| 6,174,292 B1 | 1/2001 | Kortenbach et al. |
| 6,193,671 B1 | 2/2001 | Turturro et al. |
| 6,197,007 B1 | 3/2001 | Thorne et al. |
| 6,203,527 B1 | 3/2001 | Zadini |
| 6,210,373 B1 | 4/2001 | Allmon |
| 6,217,556 B1 | 4/2001 | Ellingson et al. |
| 6,221,029 B1 | 4/2001 | Mathie et al. |
| 6,221,047 B1 | 4/2001 | Greene et al. |
| 6,224,569 B1 | 5/2001 | Brimhall |
| 6,224,576 B1 | 5/2001 | Thorne et al. |
| 6,234,773 B1 | 5/2001 | Hill et al. |
| 6,254,575 B1 | 7/2001 | Thorne, Jr. et al. |
| 6,261,242 B1 | 7/2001 | Roberts et al. |
| 6,264,617 B1 | 7/2001 | Bales et al. |
| D446,135 S | 8/2001 | Chen |
| 6,280,399 B1 | 8/2001 | Rossin et al. |
| 6,280,401 B1 | 8/2001 | Mahurkar |
| 6,280,419 B1 | 8/2001 | Vojtasek |
| 6,280,420 B1 | 8/2001 | Ferguson et al. |
| D448,314 S | 9/2001 | Chen |
| 6,283,925 B1 | 9/2001 | Terwilliger |
| 6,287,278 B1 | 9/2001 | Woehr et al. |
| 6,293,700 B1 | 9/2001 | Lund et al. |
| 6,302,852 B1 | 10/2001 | Fleming, III et al. |
| 6,309,376 B1 | 10/2001 | Alesi |
| 6,312,394 B1 | 11/2001 | Fleming, III |
| 6,315,737 B1 | 11/2001 | Skinner |
| 6,321,782 B1 | 11/2001 | Hollister |
| 6,322,537 B1 | 11/2001 | Chang |
| 6,328,701 B1 | 12/2001 | Terwilliger |
| 6,328,713 B1 | 12/2001 | Hollister |
| 6,334,857 B1 | 1/2002 | Hollister et al. |
| 6,336,915 B1 | 1/2002 | Scarfone et al. |
| 6,340,351 B1 | 1/2002 | Goldenberg |
| 6,358,252 B1 | 3/2002 | Shapira |
| 6,358,265 B1 | 3/2002 | Thorne, Jr. et al. |
| 6,361,525 B2 | 3/2002 | Capes et al. |
| 6,379,333 B1 | 4/2002 | Brimhall et al. |
| 6,379,338 B1 | 4/2002 | Garvin |
| 6,383,144 B1 | 5/2002 | Mooney |
| 6,406,459 B1 | 6/2002 | Allmon |
| 6,409,701 B1 | 6/2002 | Cohn et al. |
| 6,416,484 B1 | 7/2002 | Miller et al. |
| 6,423,034 B2 | 7/2002 | Scarfone et al. |
| 6,439,768 B1 | 8/2002 | Wu et al. |
| 6,443,910 B1 | 9/2002 | Krueger et al. |
| 6,443,927 B1 | 9/2002 | Cook |
| 6,443,929 B1 | 9/2002 | Kuracina et al. |
| 6,478,751 B1 | 11/2002 | Krueger et al. |
| 6,485,468 B2 | 11/2002 | Vojtasek |
| 6,485,473 B1 | 11/2002 | Lynn |
| 6,488,663 B1 | 12/2002 | Steg |
| 6,500,129 B1 | 12/2002 | Mahurkar |
| 6,501,384 B2 | 12/2002 | Chapman |
| 6,517,516 B1 | 2/2003 | Caizza |
| 6,519,569 B1 | 2/2003 | White et al. |
| 6,520,938 B1 | 2/2003 | Funderburk |
| 6,537,255 B1 | 3/2003 | Raines |
| 6,537,259 B1 | 3/2003 | Niermann |
| 6,544,194 B1 | 4/2003 | Kortenbach et al. |
| 6,551,287 B2 | 4/2003 | Hollister |
| 6,551,328 B2 | 4/2003 | Kortenbach |
| 6,554,778 B1 | 4/2003 | Fleming, III |
| 6,569,125 B2 | 5/2003 | Jepson et al. |
| 6,575,919 B1 | 6/2003 | Reiley et al. |
| 6,582,402 B1 | 6/2003 | Erskine |
| 6,582,446 B1 | 6/2003 | Marchosky |
| 6,585,704 B2 | 7/2003 | Luther et al. |
| 6,592,556 B1 | 7/2003 | Thorne |
| 6,595,954 B1 | 7/2003 | Luther |
| 6,595,955 B2 | 7/2003 | Ferguson et al. |
| 6,613,018 B2 | 9/2003 | Bagga et al. |
| 6,616,604 B1 | 9/2003 | Bass et al. |
| 6,616,630 B1 | 9/2003 | Woehr et al. |
| 6,623,458 B2 | 9/2003 | Woehr et al. |
| 6,626,850 B1 | 9/2003 | Chau et al. |
| D480,977 S | 10/2003 | Wawro et al. |

| | | |
|---|---|---|
| D481,321 S | 10/2003 | Knieriem et al. |
| 6,629,959 B2 | 10/2003 | Kuracina et al. |
| 6,634,789 B2 | 10/2003 | Babkes |
| 6,635,033 B1 | 10/2003 | Hill et al. |
| 6,638,252 B2 | 10/2003 | Moulton |
| 6,638,254 B2 | 10/2003 | Nakagami |
| 6,641,562 B1 | 11/2003 | Peterson |
| 6,652,486 B2 | 11/2003 | Bialecki et al. |
| 6,652,490 B2 | 11/2003 | Howell |
| 6,663,592 B2 | 12/2003 | Rhad et al. |
| 6,673,047 B2 | 1/2004 | Crawford |
| 6,673,060 B1 | 1/2004 | Fleming, III |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene et al. |
| 6,698,921 B2 | 3/2004 | Siefert |
| 6,699,221 B2 | 3/2004 | Vaillancourt |
| 6,702,786 B2 | 3/2004 | Olovson |
| 6,709,419 B2 | 3/2004 | Woehr |
| 6,719,732 B2 | 4/2004 | Courteix |
| 6,723,075 B2 | 4/2004 | Davey et al. |
| 6,727,805 B2 | 4/2004 | Hollister et al. |
| 6,730,043 B2 | 5/2004 | Krueger et al. |
| 6,731,216 B2 | 5/2004 | Ho et al. |
| 6,740,063 B2 | 5/2004 | Lynn |
| 6,749,576 B2 | 6/2004 | Bauer |
| 6,749,588 B1 | 6/2004 | Howell et al. |
| 6,749,595 B1 | 6/2004 | Murphy |
| 6,755,793 B2 | 6/2004 | Lamoureux et al. |
| 6,761,704 B2 | 7/2004 | Crawford |
| 6,761,706 B2 | 7/2004 | Vaillancourt |
| 6,764,567 B2 | 7/2004 | Sperko et al. |
| 6,767,336 B1 | 7/2004 | Kaplan |
| 6,770,050 B2 | 8/2004 | Epstein |
| 6,770,053 B2 | 8/2004 | Scarfone et al. |
| 6,796,962 B2 | 9/2004 | Ferguson et al. |
| 6,798,348 B1 | 9/2004 | Wilker et al. |
| 6,811,308 B2 | 11/2004 | Chapman |
| 6,821,267 B2 | 11/2004 | Veillon, Jr. et al. |
| 6,827,488 B2 | 12/2004 | Knieriem et al. |
| 6,832,990 B2 | 12/2004 | Kortenbach et al. |
| 6,832,992 B2 | 12/2004 | Wilkinson |
| 6,839,651 B2 | 1/2005 | Lantz et al. |
| 6,846,314 B2 | 1/2005 | Shapira |
| 6,849,051 B2 | 2/2005 | Sramek et al. |
| 6,855,128 B2 | 2/2005 | Swenson |
| 6,855,130 B2 | 2/2005 | Saulenas et al. |
| 6,860,871 B2 | 3/2005 | Kuracina et al. |
| 6,875,183 B2 | 4/2005 | Cervi |
| 6,890,308 B2 | 5/2005 | Islam |
| 6,902,546 B2 | 6/2005 | Ferguson |
| 6,916,292 B2 | 7/2005 | Morawski et al. |
| 6,916,311 B2 | 7/2005 | Vojtasek |
| 6,916,314 B2 | 7/2005 | Schneider |
| 6,923,813 B2 | 8/2005 | Phillips et al. |
| 6,936,036 B2 | 8/2005 | Wilkinson |
| D512,506 S | 12/2005 | Layne et al. |
| D512,924 S | 12/2005 | Ikeda |
| 6,976,783 B2 | 12/2005 | Chen |
| 6,981,948 B2 | 1/2006 | Pellegrino et al. |
| 6,984,213 B2 | 1/2006 | Horner et al. |
| 6,989,003 B2 | 1/2006 | Wing et al. |
| 7,008,402 B2 | 3/2006 | Ferguson et al. |
| 7,018,343 B2 | 3/2006 | Plishka |
| 7,021,824 B2 | 4/2006 | Wawro et al. |
| 7,033,324 B2 | 4/2006 | Giusti et al. |
| 7,036,984 B2 | 5/2006 | Penney et al. |
| 7,063,703 B2 | 6/2006 | Reo |
| 7,112,191 B2 | 9/2006 | Daga |
| 7,118,552 B2 | 10/2006 | Shaw |
| 7,207,973 B2 | 4/2007 | Barrelle |
| 7,226,434 B2 | 6/2007 | Carlyon et al. |
| 7,238,169 B2 | 7/2007 | Takagi et al. |
| 7,247,148 B2 | 7/2007 | Murashita |
| 7,255,475 B2 | 8/2007 | Quinn et al. |
| 7,264,613 B2 | 9/2007 | Woehr et al. |
| 7,300,420 B2 | 11/2007 | Doyle |
| 7,303,548 B2 | 12/2007 | Rhad et al. |
| 7,316,507 B2 | 1/2008 | Sisk et al. |
| 7,357,784 B2 | 4/2008 | Ferguson |
| 7,377,908 B2 | 5/2008 | Buetikofer et al. |
| 7,488,306 B2 | 2/2009 | Nguyen |
| 7,500,965 B2 | 3/2009 | Menzi et al. |
| 7,513,888 B2 | 4/2009 | Sircom |
| 2001/0021827 A1 | 9/2001 | Ferguson et al. |
| 2002/0021827 A1 | 2/2002 | Smith |
| 2003/0002562 A1 | 1/2003 | Yerlikaya et al. |
| 2003/0100868 A1 | 5/2003 | Ferguson et al. |
| 2003/0114797 A1 | 6/2003 | Vaillancourt et al. |
| 2003/0144627 A1 | 7/2003 | Woehr et al. |
| 2003/0176810 A1 | 9/2003 | Maahs et al. |
| 2003/0191438 A1 | 10/2003 | Ferguson et al. |
| 2003/0220617 A1 | 11/2003 | Dickerson |
| 2004/0071182 A1 | 4/2004 | Quinn et al. |
| 2004/0077973 A1 | 4/2004 | Groenke et al. |
| 2004/0078003 A1 | 4/2004 | Smith et al. |
| 2004/0078007 A1 | 4/2004 | Nguyen |
| 2004/0092889 A1 | 5/2004 | Ferguson et al. |
| 2004/0133167 A1 | 7/2004 | Ferguson et al. |
| 2004/0153005 A1 | 8/2004 | Krueger |
| 2004/0162526 A1 | 8/2004 | Vaillancourt |
| 2004/0171989 A1 | 9/2004 | Horner et al. |
| 2004/0186434 A1 | 9/2004 | Harding et al. |
| 2004/0225260 A1 | 11/2004 | Villa et al. |
| 2004/0236288 A1 | 11/2004 | Howell et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0054987 A1 | 3/2005 | Perez et al. |
| 2005/0070850 A1 | 3/2005 | Albrecht |
| 2005/0070851 A1 | 3/2005 | Thompson et al. |
| 2005/0070855 A1 | 3/2005 | Ferguson et al. |
| 2005/0075609 A1 | 4/2005 | Latona |
| 2005/0090763 A1 | 4/2005 | Wang |
| 2005/0090764 A1 | 4/2005 | Wang |
| 2005/0113716 A1 | 5/2005 | Mueller, Jr. et al. |
| 2005/0119652 A1 | 6/2005 | Vetter et al. |
| 2005/0131345 A1 | 6/2005 | Miller |
| 2005/0137500 A1 | 6/2005 | Wingler |
| 2005/0165404 A1 | 7/2005 | Miller |
| 2005/0192536 A1 | 9/2005 | Takagi et al. |
| 2005/0203459 A1 | 9/2005 | Alchas |
| 2005/0267383 A1 | 12/2005 | Groenke et al. |
| 2005/0273057 A1 | 12/2005 | Popov |
| 2005/0277845 A1 | 12/2005 | Cooke et al. |
| 2005/0288605 A1 | 12/2005 | Pellegrino et al. |
| 2006/0052721 A1 | 3/2006 | Dunker et al. |
| 2006/0064101 A1 | 3/2006 | Arramon |
| 2006/0116603 A1 | 6/2006 | Shibazaki et al. |
| 2006/0178625 A1 | 8/2006 | Lim et al. |
| 2006/0189934 A1 | 8/2006 | Kuracina et al. |
| 2006/0189936 A1 | 8/2006 | Carlyon et al. |
| 2006/0200195 A1 | 9/2006 | Yang |
| 2006/0276772 A1 | 12/2006 | Moos et al. |
| 2007/0110122 A1 | 5/2007 | Sisk et al. |
| 2007/0116089 A1 | 5/2007 | Bisch et al. |
| 2008/0097345 A1 | 4/2008 | Ferguson |
| 2008/0112461 A1 | 5/2008 | Bisch et al. |
| 2008/0294065 A1 | 11/2008 | Waldhoff et al. |

FOREIGN PATENT DOCUMENTS

| | | |
|---|---|---|
| EP | 1358846 A1 | 11/2003 |
| JP | 6-241914 A | 9/1994 |
| WO | 96-22800 A1 | 8/1996 |
| WO | 97-42989 A1 | 11/1997 |
| WO | 2004060138 A2 | 7/2004 |
| WO | 2004091687 A2 | 10/2004 |
| WO | 2005009246 A1 | 2/2005 |
| WO | 2005053774 A1 | 6/2005 |
| WO | WO 2005053774 A1 * | 6/2005 |
| WO | 2005060679 A2 | 7/2005 |

* cited by examiner

NEEDLE ASSEMBLY INCLUDING OBTURATOR WITH SAFETY RESET

BACKGROUND OF THE INVENTION

This invention relates generally to needle assemblies and more particularly to needle assemblies that have shields to cover sharp ends of needles.

Needle assemblies of the present invention have particular, although not exclusive application in the field of medicine and have needles with sharpened ends for use in piercing the skin to withdraw materials as needed. The needle is supported by some other structure that is used to manipulate the needle. The most common example is a syringe. However, some needle assemblies require the application of substantial force in use. One example of such a needle assembly is a bone marrow needle assembly that is used to penetrate cortical bone to reach the intramedullary canal for withdrawing liquid or a biopsy sample of bore marrow, or for infusing the canal with a selected material. Typically, the needle includes a cannula and a stylet that is received in the cannula and has a hard, sharp tip that can penetrate cortical bone. The tip projects out from the distal end of the cannula. The stylet can be withdrawn from the cannula after the needle penetrates the bone to the so that the hollow interior of the cannula can be used as a conduit for liquid or a receptacle to collect bone marrow.

In order to penetrate cortical bone, a substantial amount of force must be applied to the needle. For this reason, bone needle assemblies conventionally mount the needle in a handle that is sized and shaped so that the technician may comfortably grip the handle and apply the force necessary to penetrate the bone. The handle may comprise two handle members that can be selectively put together and separated for inserting the stylet into the cannula and removing the stylet from the cannula. A proximal handle member mounts the stylet and a distal handle member mounts the cannula. "Proximal" and "distal" refer to the relative location of the handle members to the technician when the needle assembly is in use. The proximal handle member is in contact with the palm of the technician's hand in use, and the distal handle member is on the opposite side of the proximal handle member from the palm.

Some needle assemblies, including bone needle assemblies, have associated safety mechanisms that shield the sharp tips of the needle components when they are not needed and after they have become contaminated with potentially hazardous biological material. The safety mechanism includes a shield and usually a mechanism for locking the shield in place over the sharpened tip. As a matter of convenience, and to enhance the probability that the safety feature will be used by a medical technician, the safety feature may be secured to the needle assembly. However, the safety feature must be retained out of the way when the needle assembly is being used, for example, to collect a liquid or solid sample from the intramedullary canal. The safety feature then must be released from its stowed position and moved to an operative position in which its shield covers the sharpened tip of the needle.

In cases where a sample (e.g., a bone marrow sample) is collected by the needle assembly, the sample has to be removed from the needle assembly. An obturator is a device including a long thin shaft, and in some cases includes a blunt tip, that can fit inside the cannula for pushing the sample of bone marrow out of the cannula. This can be done with the safety shield in position covering the sharp end of the cannula to protect the technician. In some cases it will be determined that the sample is not satisfactory and it will be necessary to obtain a second sample. It is not necessary to use a new needle assembly, because the needle assembly would be reused on the same patient. However, the shield is held in place over the tip of the needle assembly making it unusable for a collecting a second sample. Accordingly, there is a need for a needle assembly that can be easily reset for second use, but which will not result in inadvertent release of the safety shield. It is known to provide a key that can unlock the shield to move it away from the tip. However in order to use such a key, it is necessary to remove the obturator from the cannula to make way for the key. This makes it more difficult to reset the needle assembly for collecting a second sample.

SUMMARY OF THE INVENTION

In one aspect of the present invention, a needle assembly generally comprises mounting structure and a needle mounted on the mounting structure and extending outwardly therefrom. The needle has a longitudinal axis, a sharp end and a central axial passageway. A safety shield associated with the needle comprises a tubular housing adapted for movement relative to the needle between a stowed position in which the tubular housing is spaced from the sharp end of the needle and a deployed position in which the tubular housing covers the sharp end. A locking mechanism of the safety shield is adapted to releasably lock the tubular housing in position covering the sharp end of the needle. An obturator includes a shaft sized and shaped for reception in the central axial passageway of the needle. A reset member operatively connected to the shaft is selectively engageable with the locking mechanism of the safety shield for releasing the locking mechanism to permit the tubular housing to be move away from the sharp end of the needle.

In another aspect of the present invention, an obturator may be used with a needle assembly to remove a sample of biological material collected in the needle assembly. The needle assembly includes a safety shield having a locking mechanism capable of locking the safety shield in place on the needle assembly. The obturator generally comprises a grip for holding and manipulating the obturator and a shaft extending from the grip. The shaft is sized and shaped for reception in a central axial passageway of the needle assembly for pushing the sample out of the central axial passageway. A reset member operatively connected to the grip and adapted for engagement with the locking mechanism of the safety shield for releasing the locking mechanism.

In yet another aspect of the present invention, a method for obtaining a sample of biological material from a subject using a needle assembly and resetting the needle assembly for subsequent use, generally comprises the step of pushing a needle of the needle assembly having a central axial passageway into the subject to collect a sample of biological material from the subject in the central axial passageway. A shaft of an obturator is inserted into the central axial passageway of the needle to push the sample out of the central axial passageway. The obturator is manipulated to bring a reset member on the obturator into engagement with a locking mechanism of a shield on the needle assembly to release the locking mechanism. The shield is then moved.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
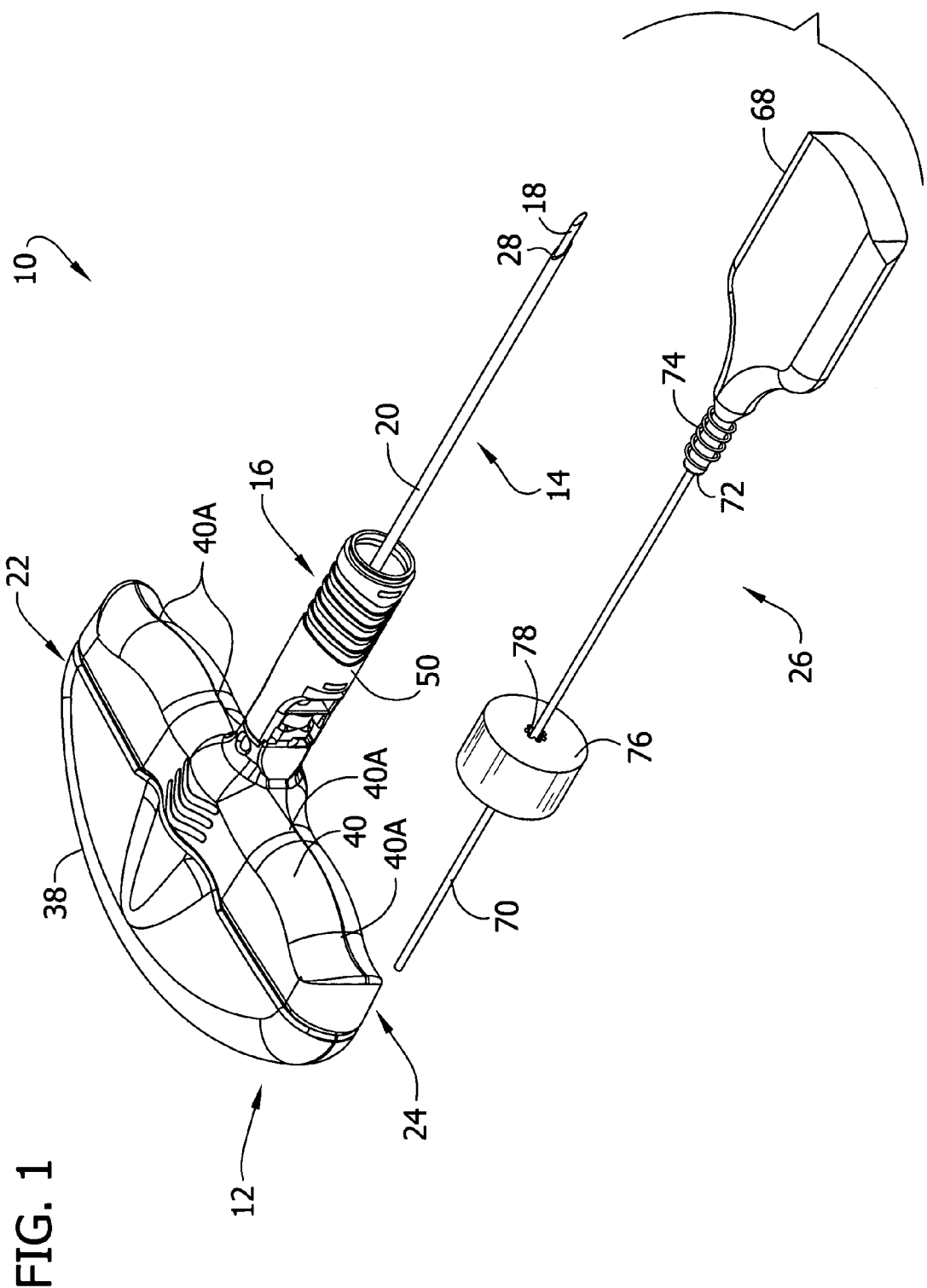
FIG. 1 is a perspective of a bone needle assembly including an obturator.

Referring now to the drawings and in particular to FIG. 1, a medical instrument constructed according to the principles of the present invention is shown in the form of a bone needle assembly, generally indicated at 10. The bone needle assembly includes a handle 12 (broadly, "mounting structure"), a needle 14 and a cannula safety shield 16, all reference numbers indicating their subjects generally. The needle 14 includes a stylet 18 and a cannula 20 that can receive the stylet. The handle 12 includes a first or proximal handle member (indicated generally at 22) mounting the stylet 18, and a second or distal handle member (indicated generally at 24) mounting the cannula 20. It will be understood that a needle could include only a single component part, or more than two parts within the scope of the present invention. Similarly, a handle could be a single part or more than two parts. The mounting structure for the needle 14 can be other than a handle without departing from the present invention. The needle assembly 10 further includes an obturator 26 (described more fully below) that may be used to remove a sample captured in the cannula 20.

The cannula 20 has a central axial passage extending the length of the cannula and opening at both ends of the cannula. A distal tip 28 of the cannula 20 is beveled and sharpened. A proximal end portion of the cannula 20 is received in the distal handle member 24. The stylet 18 is solid and includes a sharp distal tip, and a proximal end portion received in the proximal handle member 22. The stylet 18 can be inserted through the axial passage opening in the proximal end portion of the cannula 20 and received entirely through the axial passage of the cannula so that its sharp distal tip projects axially outward from the distal tip 28 of the cannula. The stylet 18 provides the tool for penetrating the cortical bone, and can be removed from the cannula 20 once the intramedullary canal is accessed by the needle 14.

The handle 12 formed by the proximal and distal handle members 22, 24 has an ergonomic shape that can be comfortably received in a medical technician's hand, and allows the technician to easily control the needle assembly 10 as he or she applies the substantial forces needed to penetrate the bone. More specifically, the top or proximal surface 38 of the proximal handle member 22 is rounded in conformance with the shape of the palm of the hand. The bottom or distal surface 40 of the distal handle member 24 is also rounded, but is undulating in shape thereby forming finger wells 40A for receiving the technician's fingers. The form of the handle can be other than described herein without departing from the scope of the present invention. The proximal and distal handle members 22, 24 can be connected together in a suitable manner when the stylet 18 is received in the cannula 20, so that the handle 12 acts essentially as a single piece when used to drive the needle 14 through a patient's skin and into the bone. The proximal and distal handle members 22, 24 can be disconnected and moved apart for removing the stylet 18 from the cannula 20.

The cannula safety shield 16 may be moved to cover the distal tip 28 of the cannula 20 after the needle assembly 10 has been used. The safety shield 16 includes a generally tubular housing 50 and an internal locking mechanism (generally indicated at 52 in FIG. 2) capable of releasably locking the tubular housing in position covering the distal tip 28 of the cannula 20. The tubular housing 50 may have any shape that is suitable for hindering access to the sharp tip 28. The tubular housing 50 need not be solid or circular in cross section within the scope of the present invention. The tubular housing 50 and handle 12 may include structure to secure the tubular housing in a retracted position adjacent the handle when not needed. An example of such structure is shown in co-assigned U.S. application Ser. No. 11/146,173, filed Jun. 6, 2005, the disclosure of which is incorporated herein by reference.

The locking mechanism 52 inside the safety shield 16 comprises a canting member including a base 56 having a hole and a pair of arms 60 (only one is shown) extending generally axially from the base. The arms 60 are connected together by a U-shaped member 62 at their ends and each has an upwardly (as oriented in the figures) bent tab 64 (only one is shown) projecting axially outward from the end. Before the locking mechanism 52 is activated to lock the tubular housing 50 in position, the ends of the arms 60 ride on the exterior surface of the cannula 20. This holds the canting member so that the base 56 is orthogonal so the longitudinal axis of the cannula 20 and the base can move along the cannula (with the safety shield 16), with the cannula sliding unimpeded through the hole in the base. Once the ends of the arms 60 pass the distal tip 28 of the cannula 20, the locking mechanism 52 is weighted so that the ends of the arms move in a generally radial direction toward an opposite side of the longitudinal axis of the needle 14. This causes the base 56 of the canting member to cant relative to the axis of the needle 14 so that the hole in the base is no longer orthogonal to the axis of the cannula. As a result, the base 56 at the edge of the hole grippingly engages the cannula 20 to lock the safety shield 16 in place. It will be understood that a locking mechanism could take on other forms than shown and described without departing from the scope of the present invention. Moreover, the canting member may take on other configurations within the scope of the present invention.

The needle assembly 10 is driven into the bone by grasping the handle 12 and pushing the stylet 18 through the skin, underlying tissue and cortical bone. Once this penetration has been achieved, the stylet 18 is no longer required. The proximal handle member 22 is disconnected from the distal handle member 24 and moved axially away from the distal handle member so that the stylet 18 slides out of the central axial passageway of the cannula 20 while the cannula remains in the bone. In order to collect a sample of bone marrow, the distal handle member is advanced further into the bone. The sharp tip 28 of the cannula 20 cuts into the bone marrow and a sample is received in the central axial passageway of the cannula. The cannula 20 can then be withdrawn from the patient by pulling on the distal handle member 24. The sample remains lodged in the central axial passageway of the cannula 20 near the sharp tip 28. It will be understood that a needle assembly may be used to collect a sample other than of bone marrow within the scope of the present invention.

Figure 2:
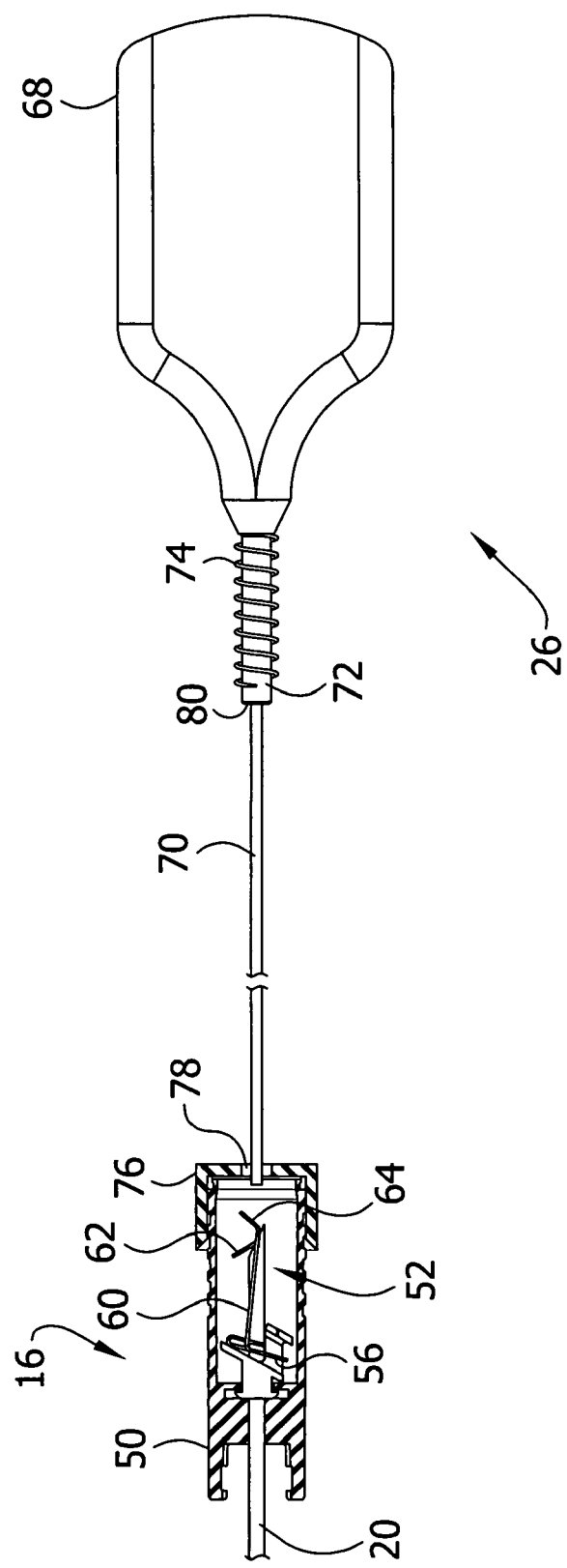
FIG. 2 is a fragmentary partial section of the needle assembly with the obturator engaging a safety shield of the needle assembly and parts broken away to show internal construction.

The obturator 26 is used to remove a lodged sample of bone marrow that has been collected in the central axial passageway of cannula 20. The obturator 26 includes a grip 68 and a long, thin shaft 70 extending from the grip that is sized to be received in the central axial passageway of the cannula 20 in generally close fitting relation therein. The grip 68 is sized and shaped to be grasped by a user for manipulating the obturator 26, as will be described. A tubular reset member 72 extends from the grip 68 in the same direction as the shaft 70 and is generally coaxial with the shaft in the illustrated embodiment. The reset member 72 has an open end 73 opposite the grip 68. A coil compression spring 74 surrounds the reset member 72 and is operatively secured to the grip 68. An annular aligning device in the form of a cap 76 is slidably mounted on the free end of the shaft 70 (opposite the grip 68), and is capable of centering the shaft relative to the tubular housing 50. In one version (not shown) the cap 76 may be attached to the spring 74 for use in retaining the cap on the obturator 26. The cap 76 has an opening 78 having an annular, resilient membrane that can engage and center the shaft 70 in the opening. As shown in FIG. 2, the cap receives a distal end portion of the tubular housing 50 in generally close-fitting relation so that the shaft 70 of the obturator 26 is aligned with the central axial passageway of the cannula 20. The cap 76 and tubular housing 50 may be formed so that the cap has a releasable, snap-acting attachment with the housing when engaging the housing. However, the attachment may be omitted or take on other forms without departing from the scope of the present invention.

Figure 3:
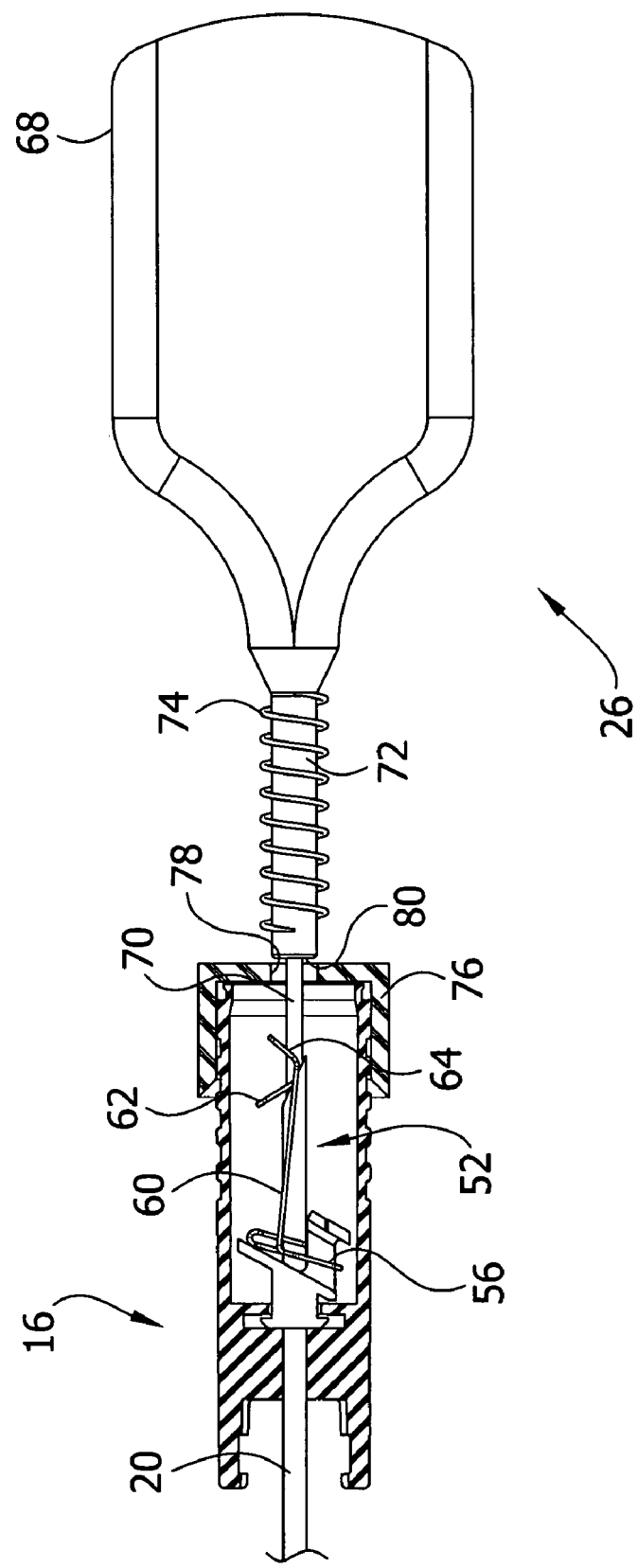
FIG. 3 is the fragmentary elevation of FIG. 2 but showing the obturator inserted to a position in which a sample collected by the needle assembly is pushed out of the needle assembly.

FIG. 2 illustrates the initial position of the obturator 26 with the cap 76 engaging the proximal end of the tubular housing 50. The free end of the shaft 70 has not yet entered the central axial passageway of the cannula 20. The grip 68 is pushed to advance the shaft 70 into the central axial passageway, which pushes the sample toward the proximal end of the central axial passageway. As shown in FIG. 3, the shaft 70 is advanced until it protrudes out of the proximal end of the central axial passageway, thereby pushing the sample (not shown) out of the cannula 20 where it can be collected in a Petri dish or other suitable container. As the shaft 70 is advanced, it slides through the cap 76. The locking mechanism 52 remains engaged so that the safety shield 16 does not move. In the position shown in FIG. 3, the spring 74 surrounding the reset member 72 engages the cap 76, but is not substantially deflected by this engagement. Thus, the technician experiences slight resistance to further inward movement of the shaft 70 into the central axial passageway of the cannula 20.

The technician may observe the sample ejected from the central axial passageway of the cannula 20. If it is determined that the sample is satisfactory, the obturator 26 can be pulled so that the shaft 70 slides back through and out of the cannula 20. The needle assembly 10 can be discarded, or possibly but less likely, cleaned and sterilized for a subsequent use. However, if the sample is not satisfactory it will be necessary to obtain a second sample. This can be done using the same needle assembly 10, but the tubular housing 50 is locked in place by the locking mechanism 52 over the sharp tip 28 of the cannula 20. The tubular housing 50 needs to be moved away from the tip 28 before the needle assembly 10 can be used to obtain a second sample.

Figure 4:
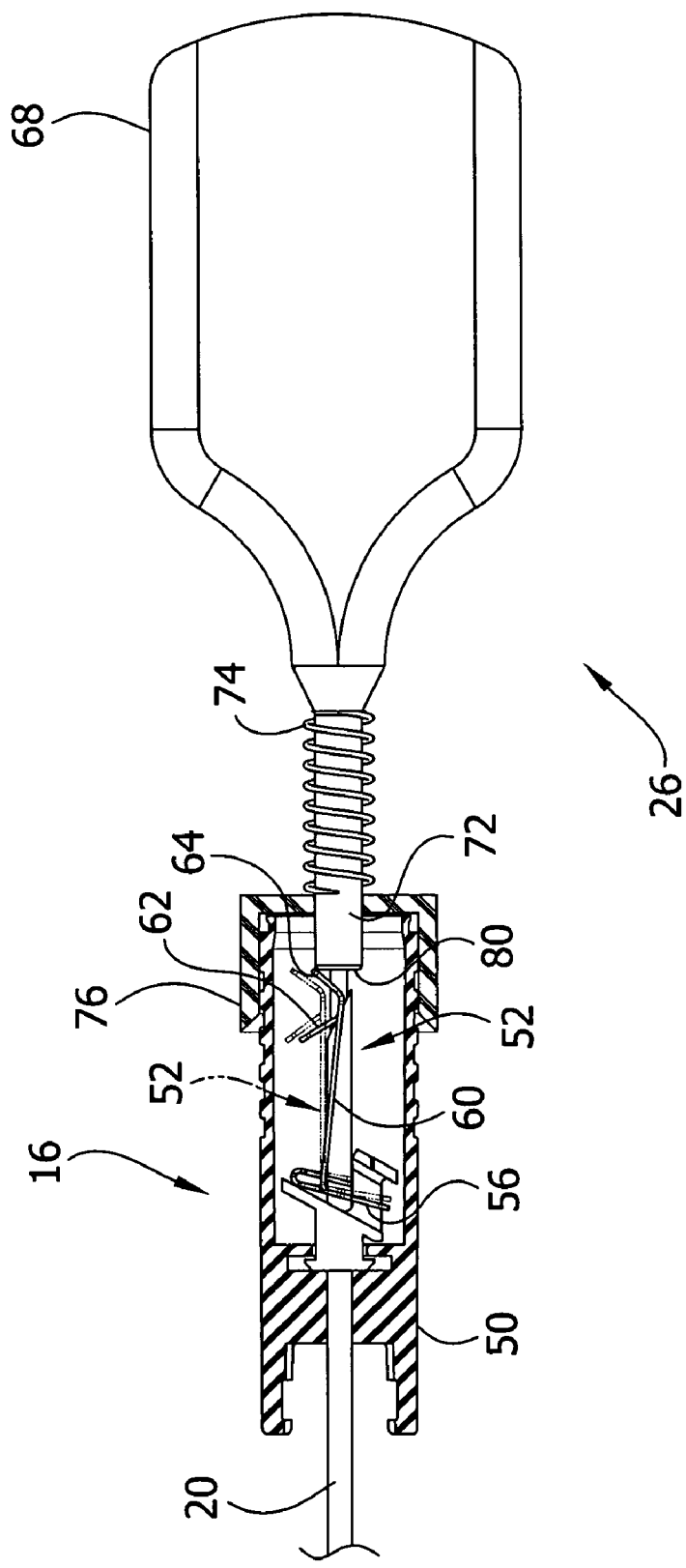
FIG. 4 is the fragmentary elevation of FIG. 2 but showing use of the obturator to reset a locking mechanism of the safety shield.
Figure 5:
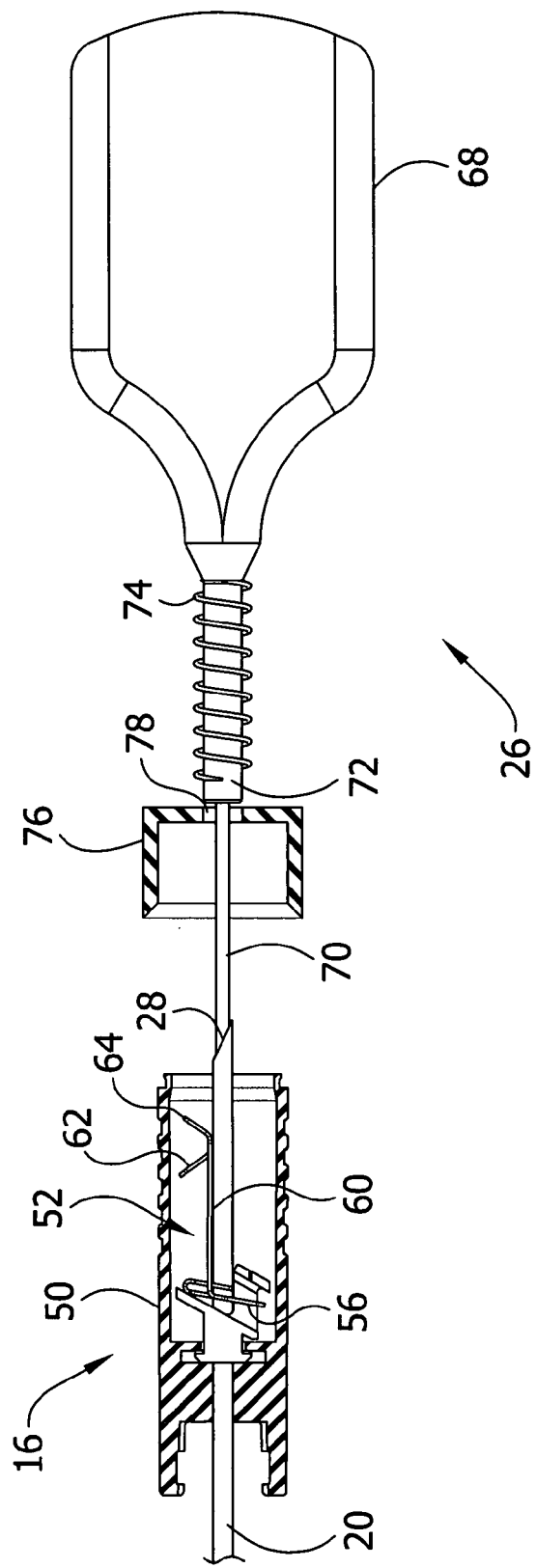
FIG. 5 is the fragmentary elevation of FIG. 2 but showing the safety shield being withdrawn from a sharp end of the needle assembly after release of the locking mechanism.
Figure 6:
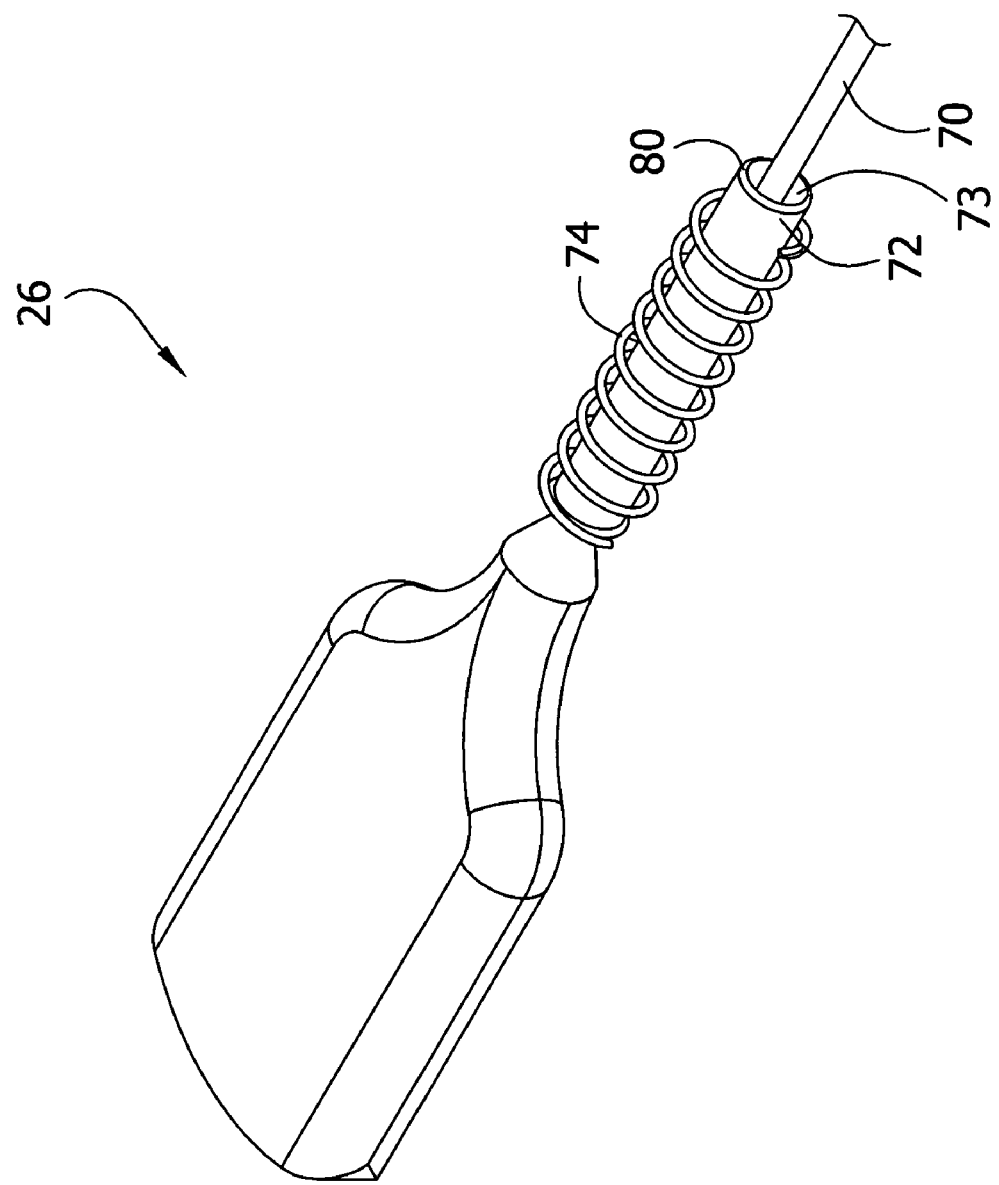
FIG. 6 is an end elevation of the obturator.
Figure 7:
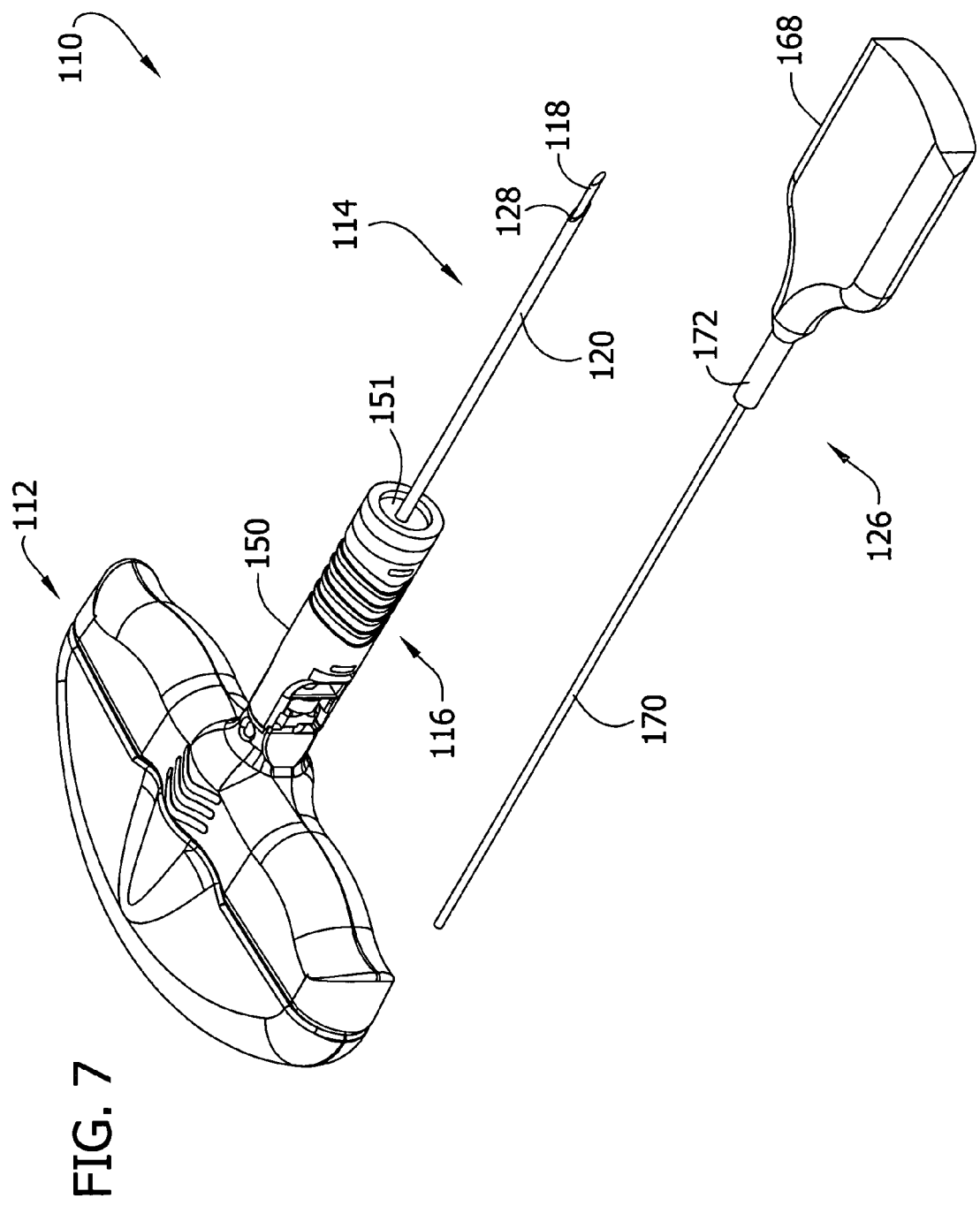
FIG. 7 is a perspective of a needle assembly of a second embodiment including an obturator.

The obturator 26 of the present invention is particularly adapted to permit the tubular housing 50 to be released and moved back from the sharp tip 28 of the cannula 20. From the position shown in FIG. 3, the grip 68 can be advanced toward the tubular housing 50 against the bias of the spring 74 so that the reset member 72 is received into the tubular housing and engages the locking mechanism 52. More particularly, the tabs 64 of the canting member engage a leading free edge portion 80 of the reset member 72 so that the reset member wedges the canting member up to a position in which the base is again substantially orthogonal to the axis of the cannula 20, as shown in phantom in FIG. 4. The open end 73 can receive a portion of the cannula 20 to allow the reset member 72 to be advanced far enough to reset the locking mechanism 52. Movement of the canting member in this manner positions the hole in the base 56 so that the cannula 20 can slide easily through the canting member. Thus as shown in FIG. 5, the tubular housing 50 can be grasped to pull back the safety shield 16 toward the distal housing member 24 so that the sharp tip 28 of the cannula 20 is once again exposed. The obturator shaft 70 can be removed and the stylet 18 can be reinserted into the cannula 20 for a second collection of a sample. It will be appreciated that the spring 74 inhibits the accidental release of the locking mechanism 52. The technician must intentionally overcome the resisting bias of the spring to de-activate the locking mechanism 52.

Referring now to FIGS. 7-11, a needle assembly 110 of a second embodiment is shown to comprise a handle 112 and a needle 114 extending from the handle. A cannula safety shield 116 received on the cannula 120 can be slid down to cover the sharp tip 128 of the cannula. The construction and operation of the handle 112 and needle 114 are substantially the same as for the handle 12 and needle 14 of the needle assembly 10 of the first embodiment. The same reference characters will be used to indicate corresponding parts of the needle assembly 110 of the second embodiment, plus "100". Moreover, the handle 112 and needle 114 will not be further described in view of their similarity to the first embodiment. The safety shield 116 includes a tubular housing 150 and a locking mechanism 152. The locking mechanism 152 may be substantially the same as the locking mechanism 52 of the first embodiment. The tubular housing 150 is similar to the tubular housing 50 of the first embodiment. However, a proximal end of the tubular housing 150 would be open except for an annular, flexible membrane 151 (broadly, "an aligning device") that covers the open end. The membrane 151 has a central aperture 153 that is aligned with the proximal opening of the central axial passageway in the cannula 120. The membrane 151 is used to guide an obturator 126 into the central axial passageway, as will be described.

The obturator 126 comprises a grip 168 and a long, thin shaft 170 extending from the grip and sized for being received in the central axial passageway of the cannula 120. The obturator 126 further includes a tubular reset member 172 projecting from the grip 168 and surrounding the portion of the shaft 170 adjacent to the grip. The construction of the obturator 126 is similar to the obturator 26 of the first embodiment, except that there is no spring 74 or annular cap 76.

Figure 8:
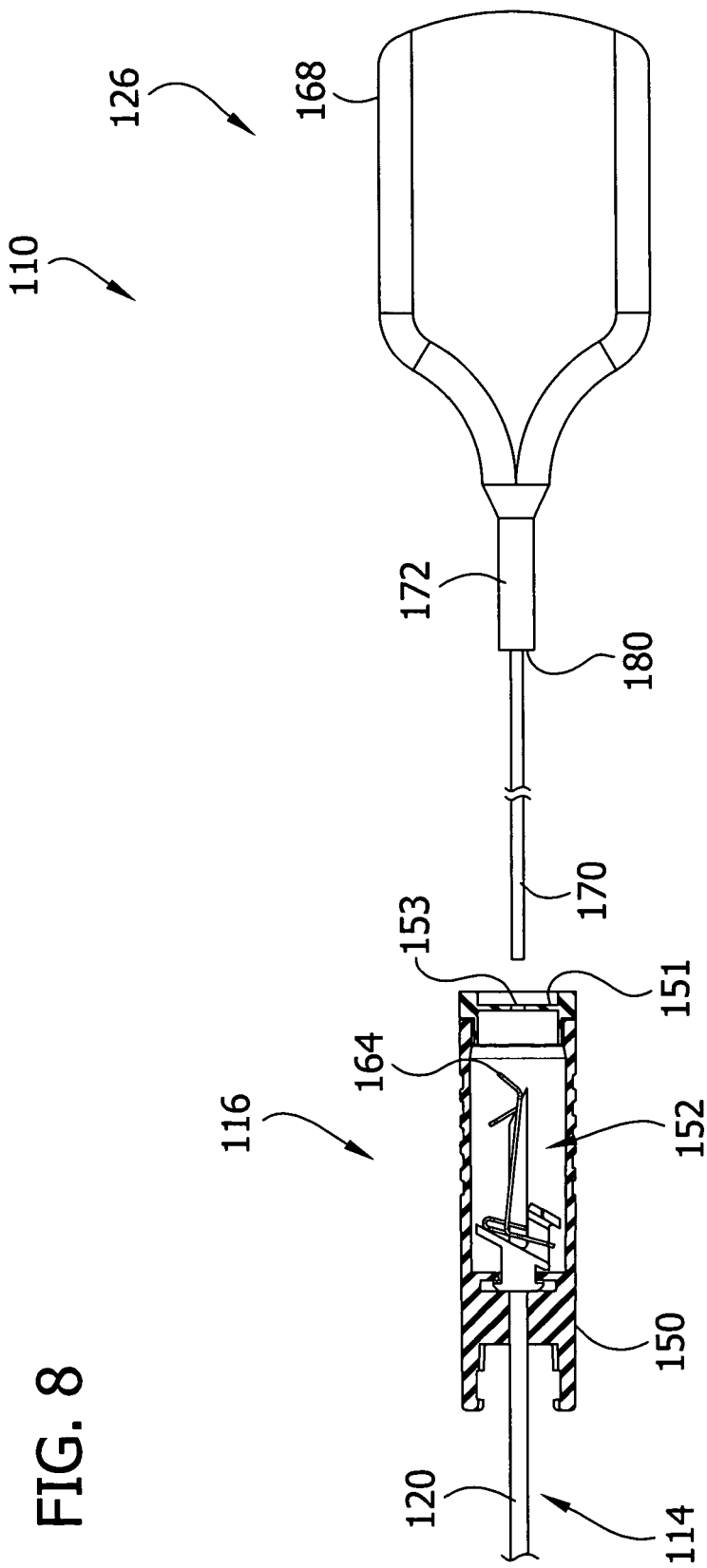
FIG. 8 is a fragmentary partial section of the needle assembly of FIG. 7 illustrating the obturator just prior to insertion into the needle assembly and parts broken away to show internal construction.
Figure 9:
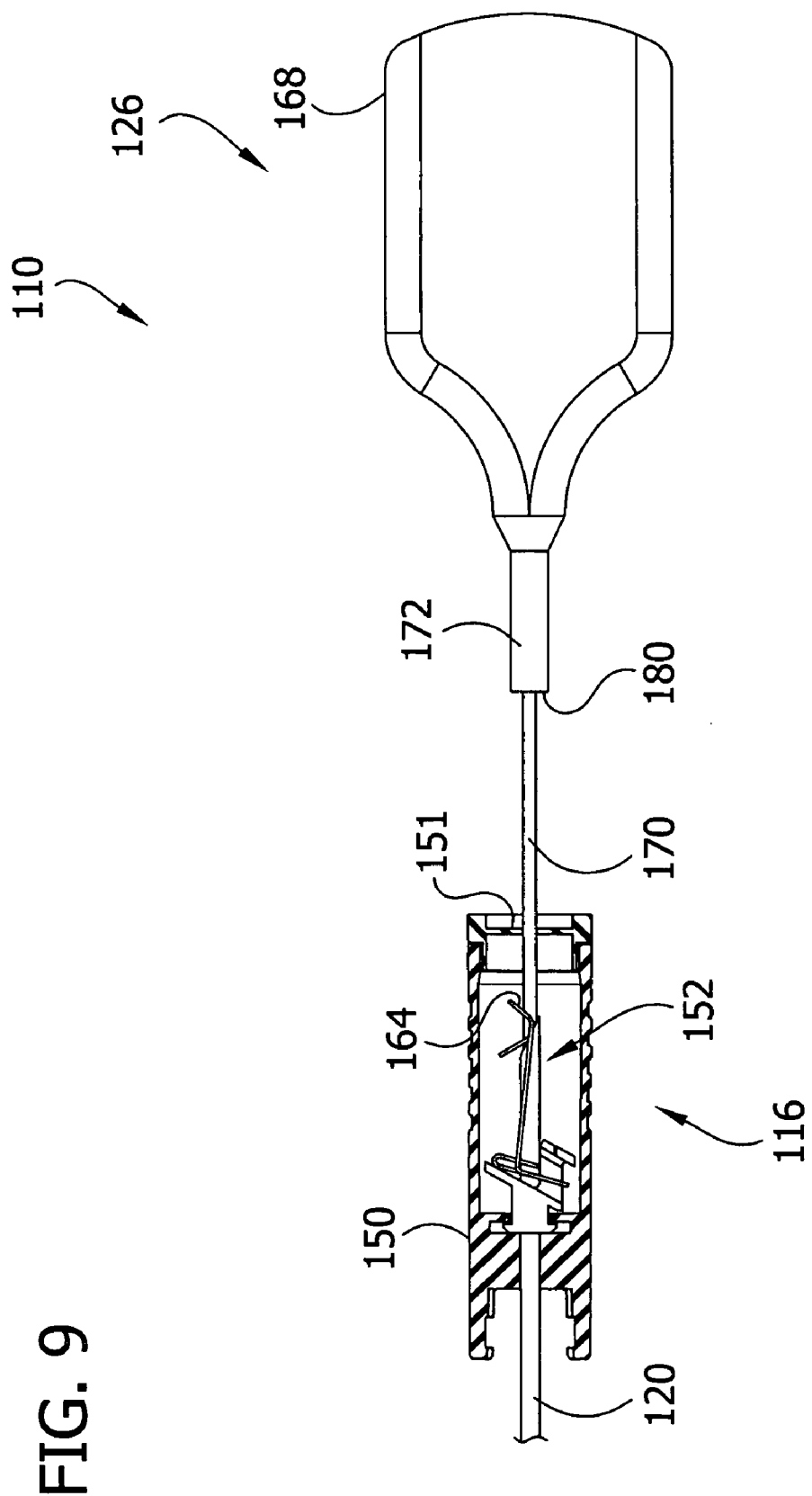
FIG. 9 is the fragmentary partial section of FIG. 8 but showing the obturator inserted into the needle assembly a distance sufficient to remove a sample from the obturator.

FIGS. 8-11 illustrate the operation of the obturator 126 of the second embodiment to remove a bone marrow sample (not shown) from the central axial passageway of the cannula 120 and, if desired, to de-activate the locking mechanism 152 of the safety shield 116 to permit the shield to be withdrawn from the sharp tip 128 of the cannula to reset the needle assembly 110 for a second use. As shown in FIG. 8, the medical technician aligns the shaft 170 with the aperture 153 in the membrane 151 of the safety shield 116, which results in the shaft also being aligned with the central axial passageway of the cannula 120. The shaft 170 is then inserted through the aperture 153 and into the central axial passageway, as shown in FIG. 9. It will be appreciated that the membrane 151 engages the shaft 170 when the shaft is inserted into the aperture 153 and thereby operates to guide the shaft into the central axial passageway. However, other structure for guiding the obturator shaft 170 may be provided, or guiding structure may be entirely omitted without departing from the scope of the present invention. The shaft 170 is sized in length so that at about the same time as a leading edge portion 180 of the reset member 172 engages the membrane 151, or slightly before, the shaft will have passed completely through the cannula 120 and project out the proximal end thereof. The sample (not shown) will have been ejected from the cannula 120 at this point. The reset member 172 may engage the membrane 151, which provides a slight resistance to further advancement of the shaft 170 into the safety shield 116 and central axial passageway of the cannula 120. This signals to the operator that the obturator 126 has been pushed far enough into the cannula 120.

Figure 10:
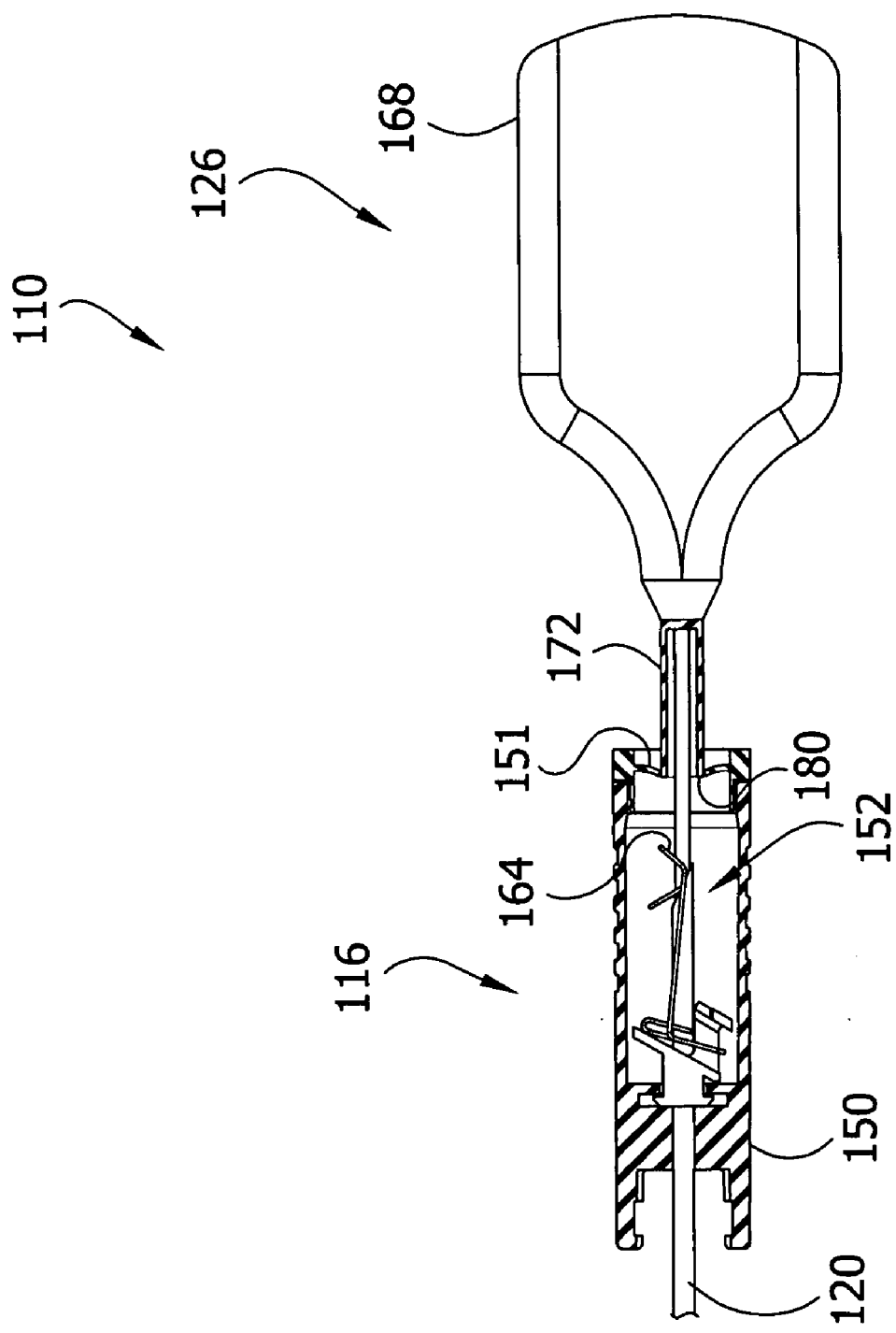
FIG. 10 is the fragmentary partial section of FIG. 8 but showing a reset feature of the obturator entering a safety shield of the needle assembly.
Figure 11:
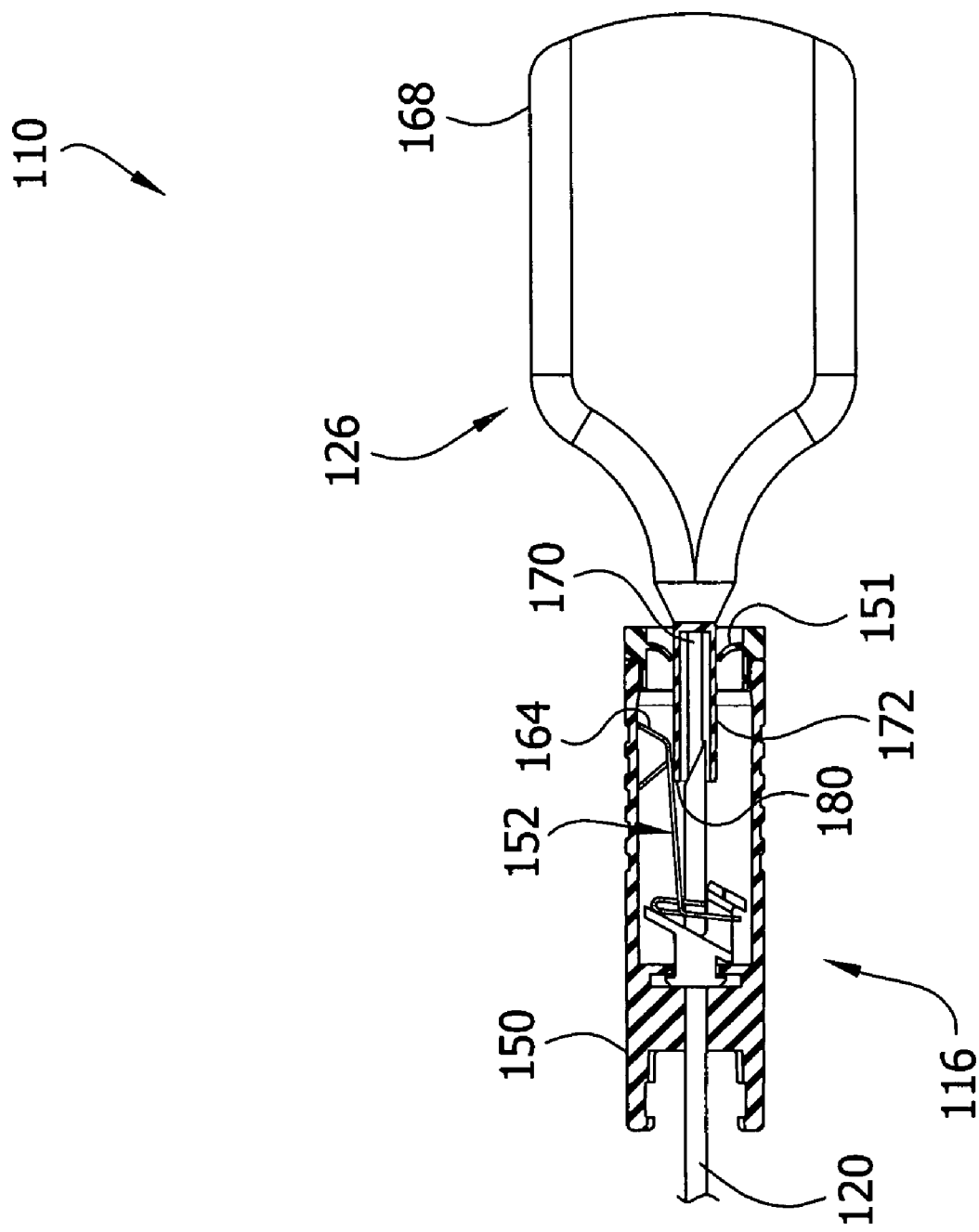
FIG. 11 is the fragmentary partial section of FIG. 8 but showing the obturator resetting a locking mechanism of the safety shield to permit the safety shield to be withdrawn from a sharp end of the needle assembly.

If the sample is satisfactory, the obturator 126 can be withdrawn from the cannula 120 and tubular housing 150, and the needle assembly 110 discarded. However, if a second bone marrow sample needs to be taken, the obturator 126 can be advanced from the position shown in FIG. 9 further into the safety shield 116. As shown in FIG. 10, the reset member 172 deflects and stretches the membrane 151, causing the aperture 153 to enlarge to the extent that the reset member 172 is admitted into the tubular housing 150 through the aperture. The reset member 172 is the only part of the obturator shown in section in FIG. 10. The reset member 172 continues to advance to the position in FIG. 11. As the reset member 172 advances, the leading edge portion 180 engages the tabs 164 of the locking mechanism 152 pushing the locking mechanism back to its position where the safety shield 116 is free to slide along the cannula 120. Thus in substantially the same was as shown in FIG. 5, the tubular housing 150 can be grasped and moved proximally away from the sharp tip 128 of the cannula 120 to ready the needle assembly 110 for a second use.

Figure 12:
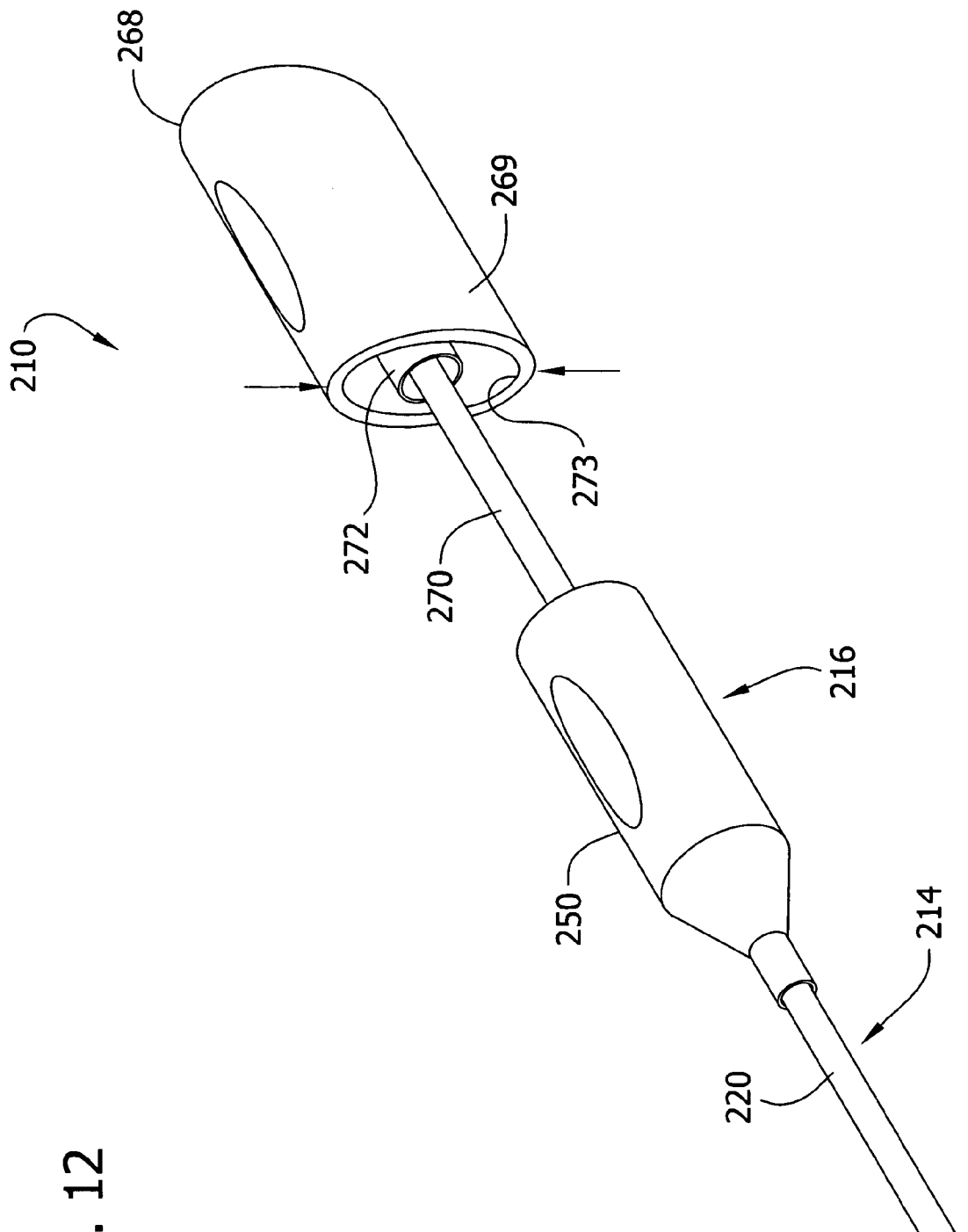
FIG. 12 is a perspective of a needle assembly of a third embodiment including an obturator.

A needle assembly 210 of a third embodiment is shown in FIG. 12. Parts of the needle assembly 210 of the third embodiment are indicated by the same reference numerals as for the needle assembly 10 of the first embodiment, plus "200". The obturator 226 includes a grip 268 having a generally tubular portion 269 that extends along the shaft 270 to a distance which fully surrounds the reset member 272. The cross section of an opening 273 defined by the tubular portion 269 of the grip 268 is elliptical (or otherwise not the same shape as the cross section of the tubular housing 250). The shaft 270 may be inserted into the tubular housing 250 and central axial passageway of the cannula 220 as before. However when the grip 268 reaches the tubular housing 250, it engages the tubular housing because the elliptical cross sectional shape of the opening 273 does not match the circular cross sectional shape of the tubular housing. This prevents the reset member 272 from being inadvertently inserted into the tubular housing 250 resulting in an unintended release of the locking mechanism 252 which could cause the contaminated sharp tip 228 of the cannula 220 to be exposed when the obturator 226 is removed from the central axial passageway.

If it is necessary to de-activate the locking mechanism 252 and withdraw the safety shield 216 from the sharp tip (not shown) of the cannula 220, the obturator 226 can be reconfigured so that the reset member 272 can move into the tubular housing 250. This can be accomplished by squeezing on opposite sides of the grip 268, such as indicated by the arrows in FIG. 12. For instance, the points at which the grip 268 is engaged for squeezing may be the opposite ends of the major axis of the ellipse. The grip 268 is formed of an elastic and resilient material that allows the elliptical shape of the opening 273 to become more nearly circular to match the shape of the tubular housing 250. Once the shapes are matched, the grip 268 and reset member 272 can be advanced, with the grip receiving the tubular housing 250 therein and the tubular housing receiving the reset member 272. The reset member operates to de-activate the locking mechanism 252 in the same way as described previously herein.

Figure 13:
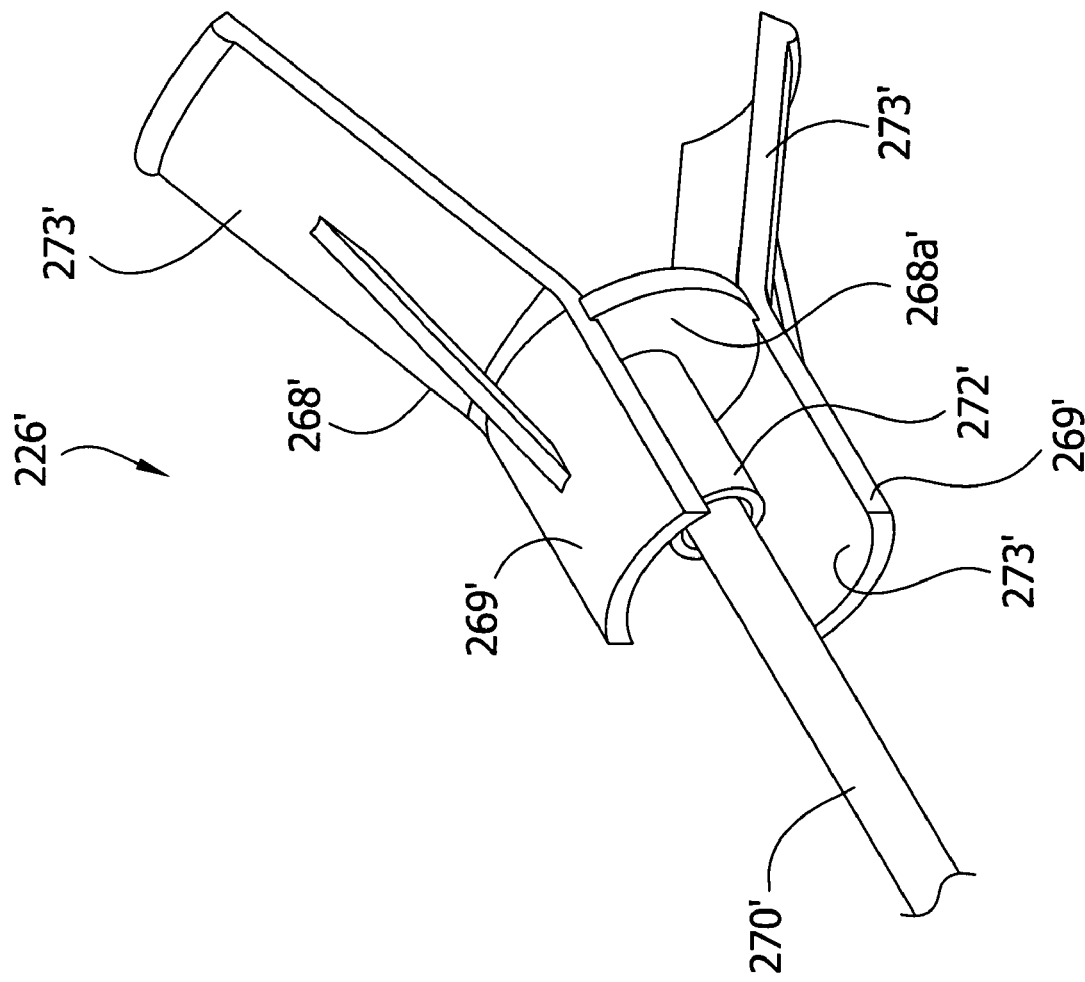
FIG. 13 is a perspective of a modified obturator similar to that of FIG. 12.
Figure 14:
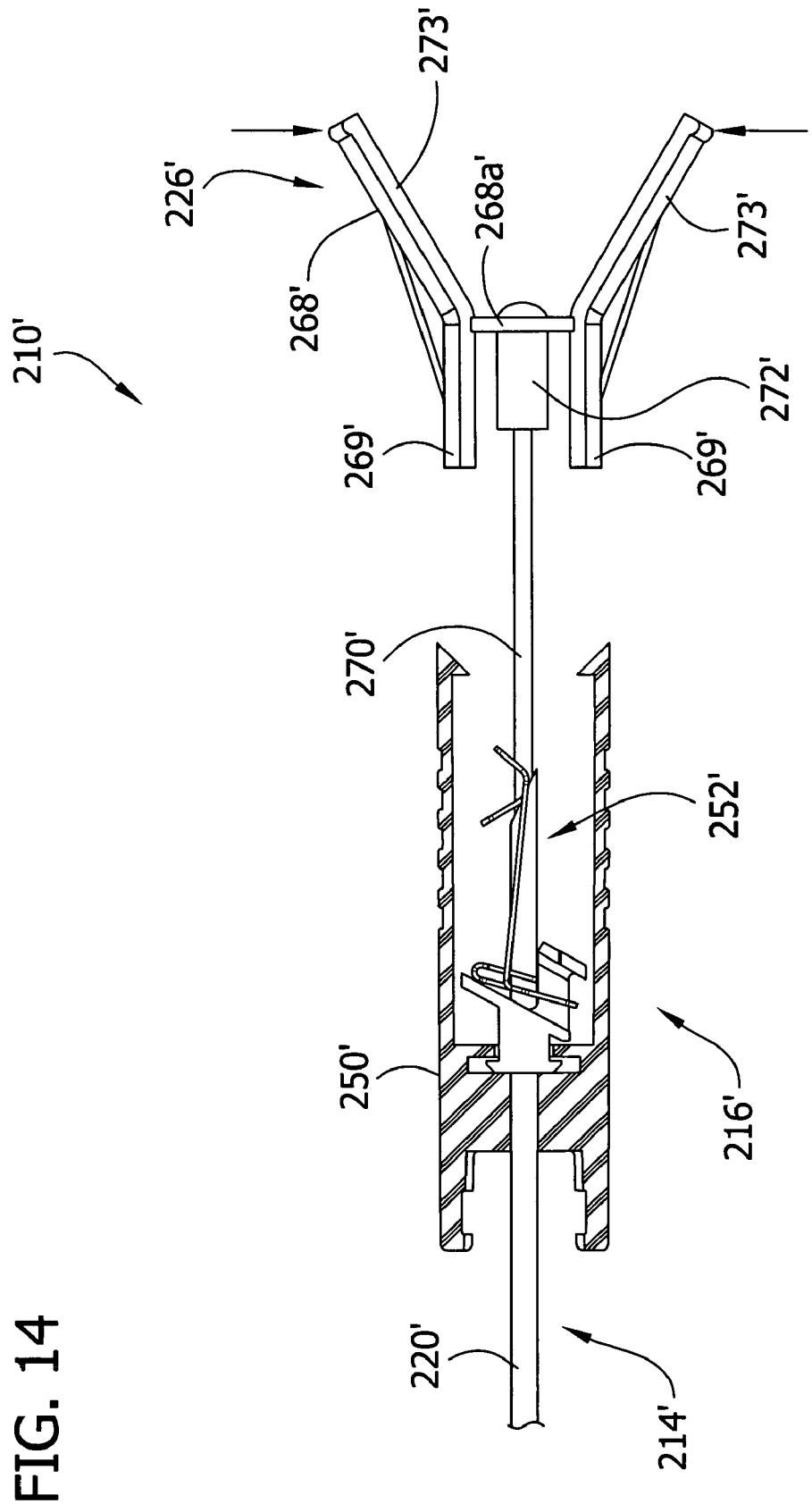
FIG. 14 is a fragmentary partial section showing the obturator of FIG. 13 inserted into the needle assembly but prior to resetting a locking mechanism thereof with parts broken away to show internal construction.

Referring now to FIGS. 13 and 14, a modified obturator 226' of the second embodiment is shown. The same reference numerals as used for the needle assembly 210 of the third embodiment will be used to indicate corresponding parts in the modified version, with the addition of a trailing prime. It is noted that the tubular housing 250' of the safety shield 216' does not include the membrane 151 of the second embodiment, but otherwise may be of the same construction. However, a membrane (not shown) could be employed in this modified version. The principle of operation is similar to the third embodiment. More specifically the grip 268' includes a circular base 268a' from which two projecting members 269' extend a distance greater than the axial extent of the reset member 272'. The projecting members 269' at their free ends are spaced apart across an opening 273' a distance less than the diameter of the tubular housing 250', but are not sized to fit inside the tubular housing. Accordingly when the obturator shaft 270' is inserted into the central axial passageway of the cannula 220' a distance which brings the grip 268' into engagement with the tubular housing 250', the free ends of the projecting members 269' engage the tubular housing and prevent further advancement. Thus, the reset member 272' remains outside the tubular housing 250' and the locking mechanism 252' is not inadvertently de-activated.

To allow the locking mechanism 252' to be de-activated and the safety shield 216' withdrawn from the sharp tip of the cannula 220, the grip 268' is provided with wings 273', each projecting outward from the base 268a' adjacent to a respective one of the projecting members 269'. The wings extend generally in the opposite direction from the base 268a' as the projecting members 269', but also extend radially outward so that the wings 273' diverge from each other. The wings 273' can be gripped and squeezed as indicated in FIG. 14 so that the free ends of the projecting members 269' move apart from each other. The base 268a' acts as the fulcrum about which the projecting members 269' pivot. This movement allows the projecting members 269' to receive the tubular housing 250' between them. The reset member 272' can be advanced into the tubular housing 250' to de-activate the locking mechanism 252' as described previously herein.

Figure 15:
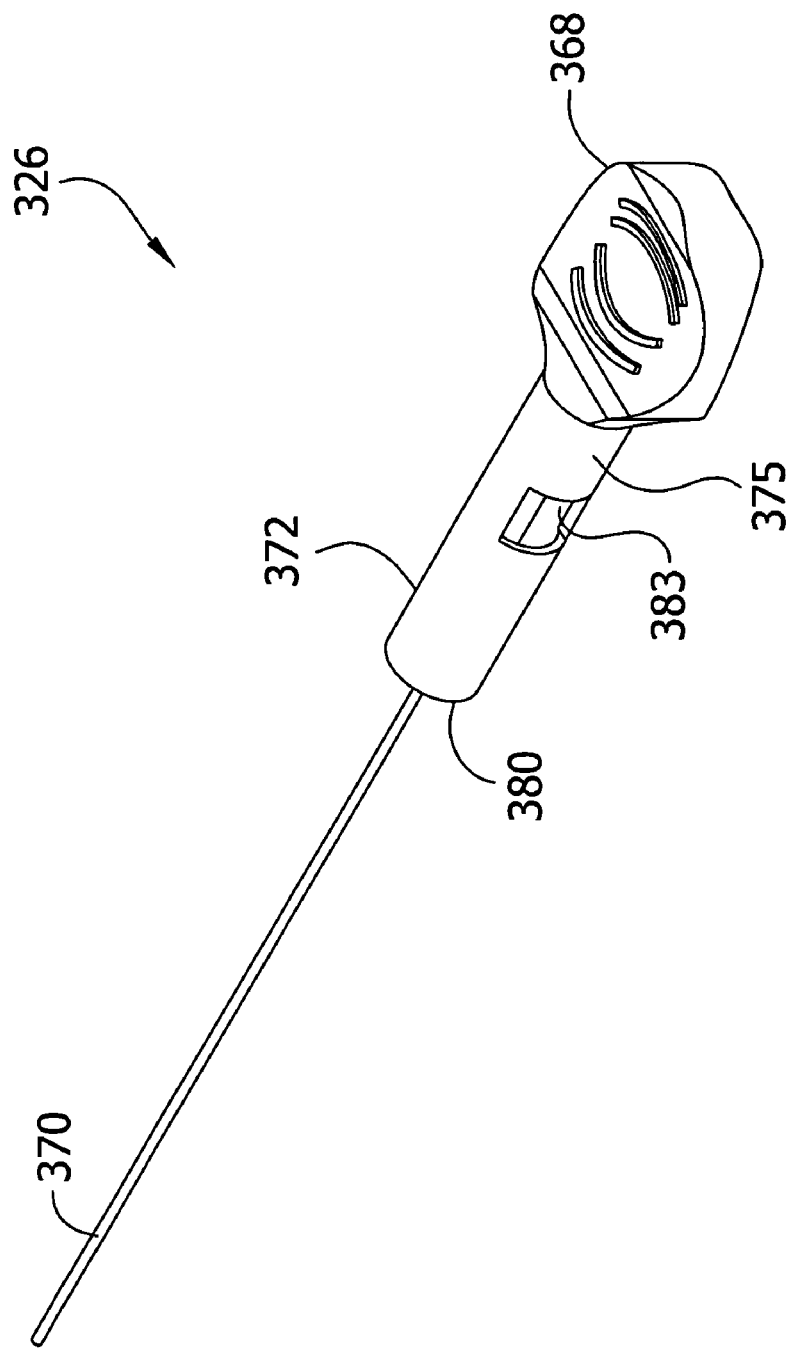
FIG. 15 is a perspective of an obturator of a needle assembly of a fourth embodiment.
Figure 16:
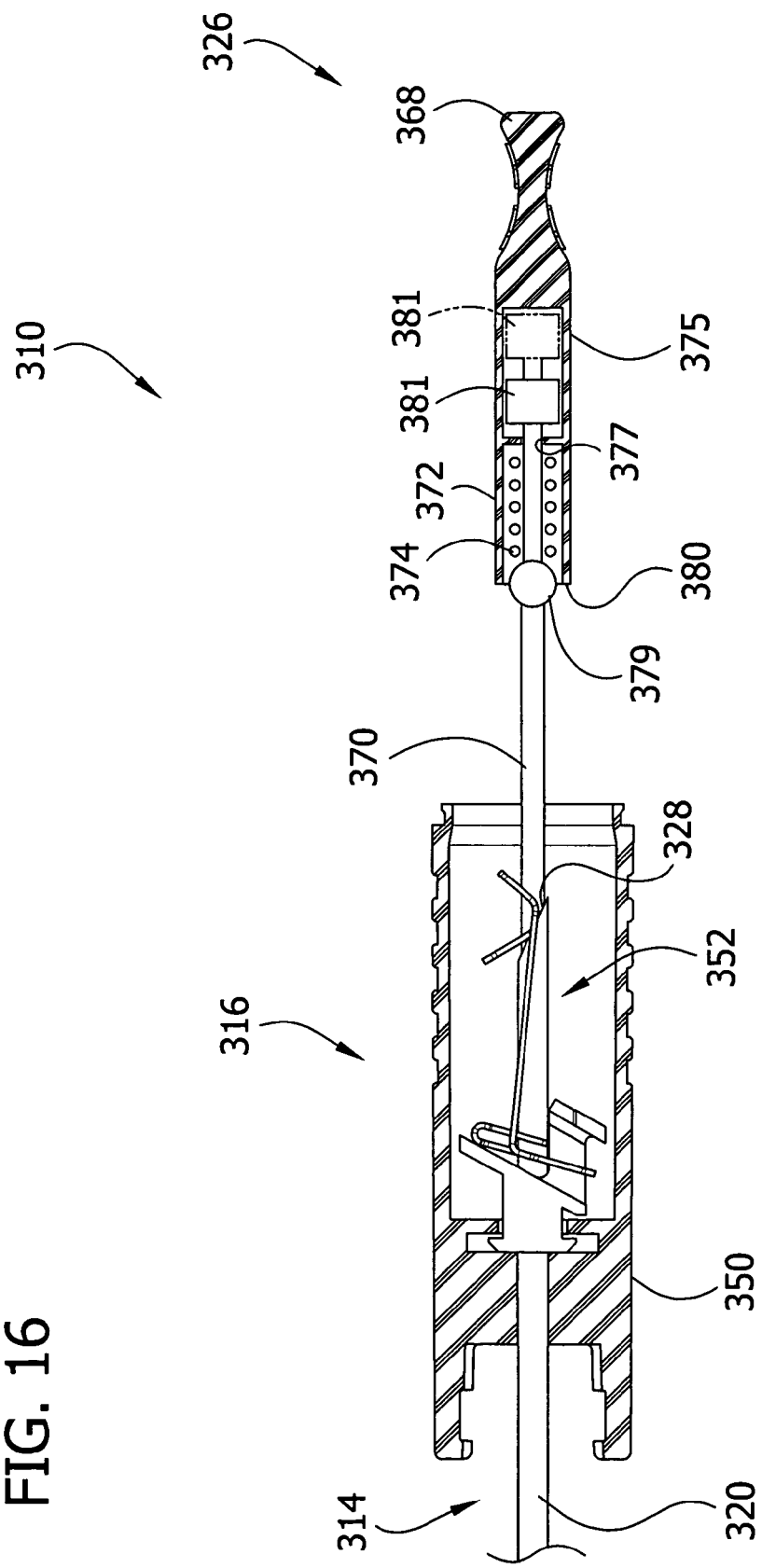
FIG. 16 is a fragmentary partial section of the obturator partially inserted into the needle assembly with parts broken away to show internal construction.

Referring now to FIGS. 15 and 16, a needle assembly 310 of a fourth embodiment includes component parts that are indicated by the same reference numerals as used for the needle assembly 10 of the first embodiment, plus "300". The needle 314 and safety shield 316 shown in FIG. 16 may have the same construction and operation as the corresponding parts in the embodiment shown in FIG. 14. The obturator 326 of the fourth embodiment includes a grip 368 and a hollow cylindrical portion 375 extending axially from the grip. The reset member 372 is located on the axially opposite side of the hollow portion 375 from the grip 368. A hole 377 in the hollow portion 375 allows its interior to communicate with the interior of the tubular reset member 372. The shaft 370 includes an obstruction 379 positioned adjacent the free edge portion 380 of the reset member 372. The shaft 370 extends through the reset member 372 and the hole 377 into the hollow portion 375. The end of the shaft 370 is formed with an indicator plaque 381 that is wider than the hole 377 in the hollow portion 375 so that the shaft 370 may not be withdrawn from the hollow portion. It will be understood that the plaque 381 may have other shapes (e.g., cylindrical with a larger diameter than the hole 377) without departing from the scope of the present invention. The shaft 370 may be moved axially relative to the reset member 372 and hollow portion 375. A coil compression spring 374 is located in the tubular reset member 372. The spring bears against a wall around the hole 377 that separates the interior of the reset member 372 from the interior of the hollow portion 375. The other end of the spring 374 bears against the obstruction 379 on the shaft 370. Thus, the spring 374 biases the shaft 370 axially outwardly from the grip 368, hollow portion 375 and reset member 372.

The hollow portion 375 includes a window 383 defined in the hollow portion 375 that is transparent or translucent. The window could be formed simply by an opening in the hollow portion. The other parts of the hollow portion 375 are opaque. Thus, when the plaque 381 is in the position shown in solid lines in FIG. 16, it cannot be seen through the window 383. However as will be described, the shaft 370 can be moved to bring the plaque 381 into registration with the window 383 so that the plaque is visible through the window. The plaque 381 may be colored to increase its visibility.

In operation to remove a bone marrow sample from the cannula 320, the shaft 370 is aligned with the central axial passage of the cannula and inserted. Although no alignment device is shown, a cap like the cap 76 shown in FIG. 1, a membrane like the membrane 151 shown in FIG. 8, or some other suitable aligning device can be used to assist getting the shaft 370 inside the central axial passageway can be used. The shaft 370 can be easily advanced through the central axial passageway of the cannula 320 until the obstruction 379 engages the distal end of the cannula. The obstruction 379 is too large to fit into the central axial passageway and so resistance to further advancement of the shaft 370 into the cannula 320 is felt by the medical technician. The shaft 370 is sized so that at this point the shaft extends completely through the cannula 320 and the sample (not shown) will have been ejected.

If it is necessary to reset the needle assembly 310 for collecting another bone marrow sample, then the obturator 326 can be advanced against the bias of the spring 374. This allows the reset member 372 to enter the tubular housing 350 of the safety shield 316 for engaging the locking mechanism 352 to de-activate it as described previously. However, the shaft 370 remains stationary relative to the cannula 320 because of the engagement of the obstruction 379 with the cannula. This causes the plaque 381 to move relative to the hollow portion 375 so that it is brought into registration with the window 383 (shown in phantom in FIG. 16). The appearance of the plaque 381 indicates that the reset member 372 has been inserted far enough to de-activate the locking mechanism 352. The technician is given visual confirmation that de-activation has occurred so that he or she knows that the safety shield 316 can be withdrawn (i.e., substantially as shown in FIG. 5). It will be understood that other ways of confirming de-activation of the locking mechanism 352 can be used within the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A needle assembly comprising:

mounting structure;

a tubular needle mounted on the mounting structure and extending outwardly therefrom, the needle having a longitudinal axis, a sharp end and a central axial passageway;

a safety shield associated with the needle and comprising a tubular housing adapted for movement relative to the needle between a stowed position in which the tubular housing is spaced from the sharp end of the needle and a deployed position in which the tubular housing covers the sharp end, and a locking mechanism adapted to releasably lock the tubular housing in position covering the sharp end of the needle; and an obturator including a shaft sized and shaped to be received in the central axial passageway of the needle, a reset member operatively connected to the shaft, disposed relative to the shaft so movement of the shaft in a direction into the central axial passageway can bring the reset member into engagement with the locking mechanism to release the locking mechanism, and selectively engageable with the locking mechanism of the safety shield for releasing the locking mechanism to permit the tubular housing to move away from the sharp end of the needle, and a grip for gripping the obturator, the shaft and reset member extending from the grip in the same direction, the reset member includes a tube extending from the grip and having an open end opposite the grip, the obturator shaft extending through the tube to the grip.

2. A needle assembly as set forth in claim 1 further comprising an aligning device for aligning the shaft of the obturator with the central axial passageway of the needle.

3. A needle assembly as set forth in claim 2 wherein the tubular housing has an open end, and wherein the aligning device comprises an annular membrane substantially covering the open end of the tubular housing, the annular membrane having an aperture generally aligned with the central axial passageway for guiding the shaft of the obturator into the central axial passageway.

4. A needle assembly as set forth in claim 2 wherein the aligning device comprises a cap including an aperture sized and shaped for receiving the obturator shaft therethrough, the cap being adapted for engagement with the tubular housing to generally align the aperture with the central axial passage of the needle.

5. A needle assembly comprising:
mounting structure;
a tubular needle mounted on the mounting structure and extending outwardly therefrom, the needle having a longitudinal axis, a sharp end and a central axial passageway;
a safety shield associated with the needle having a tubular housing adapted for movement relative to the needle between a stowed position in which the tubular housing is spaced from the sharp end of the needle and a deployed position in which the tubular housing covers the sharp end, and a locking mechanism adapted to releasably lock the tubular housing in position covering the sharp end of the needle;
an obturator including a shaft sized and shaped to be received in the central axial passageway of the needle, and a reset member operatively connected to the shaft and selectively engageable with the locking mechanism of the safety shield for releasing the locking mechanism to permit the tubular housing to move away from the sharp end of the needle; and
a reset inhibitor associated with the shaft and engageable with the needle upon insertion of the obturator shaft into the central axial passageway to inhibit inadvertent release of the locking mechanism, said reset inhibitor including a projecting portion extending around the reset member, the projecting portion defining an opening having a first shape in a first configuration that differs from a shape of the tubular housing, and having a second shape in a second configuration so that the tubular housing can be received in the projecting portion in the second configuration.

6. A needle assembly as set forth in claim 5 wherein the reset inhibitor comprises a resilient member engageable with the needle assembly to yieldably resist movement of the reset member into the tubular housing.

7. A needle assembly as set forth in claim 6 wherein the reset inhibitor further comprises an obstruction on the shaft sized larger than a cross sectional area of the central axial passageway and engageable with the needle to prevent further insertion of the shaft into the central axial passageway.

8. A needle assembly as set forth in claim 5 wherein the projecting portion includes at least two spaced apart projecting members.

9. A needle assembly comprising:
mounting structure;
a tubular needle mounted on the mounting structure and extending outwardly therefrom, the needle having a longitudinal axis, a sharp end and a central axial passageway;
a safety shield associated with the needle having a tubular housing adapted for movement relative to the needle between a stowed position in which the tubular housing is spaced from the sharp end of the needle and a deployed position in which the tubular housing covers the sharp end, and a locking mechanism adapted to releasably lock the tubular housing in position covering the sharp end of the needle;
an obturator including a shaft sized and shaped to be received in the central axial passageway of the needle, and a reset member operatively connected to the shaft and selectively engageable with the locking mechanism of the safety shield for releasing the locking mechanism to permit the tubular housing to move away from the sharp end of the needle; and
a status indicator mounted on the shaft of the obturator adapted to show when the reset member has released the locking mechanism.

10. A needle assembly as set forth in claim 9 wherein the obturator includes a window, the status indicator being adapted to be aligned with the window when the reset member releases the locking mechanism.

* * * * *